US008703439B1

(12) United States Patent
Lester

(10) Patent No.: US 8,703,439 B1
(45) Date of Patent: Apr. 22, 2014

(54) POINT OF CARE IODINE SENSOR

(76) Inventor: Linda Lester, Portland, OR (US)

( * ) Notice: Subject to any disclaimer, the term of this patent is extended or adjusted under 35 U.S.C. 154(b) by 0 days.

(21) Appl. No.: 13/523,580

(22) Filed: Jun. 14, 2012

Related U.S. Application Data

(63) Continuation of application No. 13/363,295, filed on Jan. 31, 2012, now abandoned.

(60) Provisional application No. 61/438,115, filed on Jan. 31, 2011.

(51) Int. Cl.
*C12Q 1/28* (2006.01)
*C12N 9/00* (2006.01)
*C12N 1/20* (2006.01)
*C12N 15/00* (2006.01)
*C07H 21/04* (2006.01)

(52) U.S. Cl.
USPC ....... 435/28; 435/183; 435/252.3; 435/320.1; 536/23.2

(58) Field of Classification Search
None
See application file for complete search history.

(56) References Cited

U.S. PATENT DOCUMENTS

| | | | |
|---|---|---|---|
| 4,275,149 A | 6/1981 | Litman et al. |
| 4,313,734 A | 2/1982 | Leuvering |
| 4,373,932 A | 2/1983 | Gribnau et al. |
| 4,889,427 A | 12/1989 | Van Veen et al. |
| 4,954,452 A | 9/1990 | Yost et al. |
| 4,996,143 A | 2/1991 | Heller et al. |
| 6,670,113 B2 | 12/2003 | Hainfeld |
| 6,921,496 B2 | 7/2005 | Anderson et al. |
| 7,593,110 B2 | 9/2009 | Feng et al. |
| 7,671,995 B2 | 3/2010 | Lin et al. |
| 7,701,582 B2 | 4/2010 | Sadowski |
| 7,705,990 B2 | 4/2010 | Thrush et al. |
| 7,723,122 B2 | 5/2010 | Tsuzuki |
| 7,754,493 B2 | 7/2010 | Tsuzuki |
| 7,791,730 B2 | 9/2010 | Lee et al. |
| 7,846,396 B2 | 12/2010 | Roitman et al. |
| 8,060,328 B2 | 11/2011 | Tracy |
| 8,094,316 B1 | 1/2012 | Homola et al. |
| 2004/0265922 A1 | 12/2004 | Bieniarz et al. |
| 2005/0100976 A1 | 5/2005 | Bieniarz et al. |
| 2009/0103851 A1 | 4/2009 | Tsao et al. |
| 2010/0128273 A1 | 5/2010 | Lee et al. |
| 2010/0248209 A1 | 9/2010 | Datta et al. |

FOREIGN PATENT DOCUMENTS

| | | |
|---|---|---|
| WO | WO 98/39657 | 9/1998 |
| WO | WO 2004/078976 | 9/2004 |
| WO | WO 2005/003777 | 1/2005 |

OTHER PUBLICATIONS

Whisstock et al. Q Rev Biophys. Aug. 2003;36(3):307-40.*
Chica et al. Curr Opin Biotechnol. Aug. 2005;16(4):378-84.*
Sen et al. Appl Biochem Biotechnol. Dec. 2007;143(3):212-23.*
Abraham et al., "Measurement of urinary iodide levels by ion-selective electrode: improved sensitivity and specificity by chromatography on anion-exchange resin," *The Original Internist*, pp. 19-32, Dec. 2004.
Adak et al., "An essential role of active site arginine residue in iodide binding and histidine residue in electron transfer for iodide oxidation by horseradish peroxidase," *Molecular and Cellular Biochemistry*, 218:1-11, 2001.
Als et al., "Quantification of urinary iodine: a need for revised thresholds," *European Journal of Clinical Nutrition*, 57:1181-1188, 2003.
Amachi et al., "Hydrogen peroxide-dependent uptake of iodine by marine Flavobacteriaceae bacterium strain C-21," *Applied and environmental microbiology*, 2007;73(23):7536-41.
Benoist, "Iodine deficiency in 2007: Global progress since 2003," *Food and Nutrition Bulletin*, 29:195-202, 2008.
Colin et al., "Vanadium-dependent iodoperoxidases in Laminaria digitata, a novel biochemical function diverging from brown algal bromoperoxidases,"*J. Biological Inorganic Chemistry*, 10(2):156-66, 2005.
Dixneuf et al., "The time dependence of molecular iodine emission from *Laminaria digitata*," *Atmosph. Chem. and Physics*, 9:823-829, 2009.
Fan et al. "Sensitive optical biosensors for unlabeled targets: a review," *Analytica Chimica Acta*., 620:8-26, 2008.
Gnat et al., "Fast colorimetric method for measuring urinary iodine," *Clin. Chem.*, 49:186-188, 2003.
Harden and Bastomsky, "Measurement of iodine concentration in biological material," *Clinical Chemistry*, 17:1020-1023, 1971.
Kohn et al., "Engineering a signal transduction mechanism for protein-based biosensors," Proc. Nat'l. Acad. Sci. USA, 102:10841-10845, 2005.
Leblanc et al., "Iodine transfers in the coastal marine environment: the key role of brown algae and of their vanadium-dependent haloperoxidases," *Biochimie*, 88:1773-85, 2006.
Martin-Palma et al., "Optical biosensors based on semiconductor nanostructures," *Sensors*, 9:5149-5172, 2009.
Park et al., "Conformational changes of calmodulin upon Ca2+ binding studied with a microfluidic mixer," *Proc. Natl. Acad. Sci. USA*, 105(2):542-7, 2008.
Ristic-Medic et al., Methods of assessment of iodine status in humans: a systematic review, *Am. J. Clin. Nutr.*, 89(suppl):2052-69, 2009.
Springer et al., "Real-time monitoring of bimolecular interactions in blood plasma using a surface Plasmon resonance biosensor," *Analytical and Bioanalytical Chemistry*, 398:1955-1961, 2010.
Vaillancourt et al., "Nature's inventory of halogenation catalysts: oxidative strategies predominate," *Chem. Rev.*, 106:3364-3378, 2006.

(Continued)

*Primary Examiner* — Christian Fronda
(74) *Attorney, Agent, or Firm* — Klarquist Sparkman, LLP

(57) ABSTRACT

Methods and devices for use in detecting the iodine status of a subject are provided. The methods and devices utilize an iodide binding protein (IBP) to specifically bind to and facilitate detection of iodide in a saliva sample from a subject. The detected iodide can be used to detect the iodide status of the subject. In several examples, the IBP includes an iodide binding domain from a vanadium dependent iodoperoxidase (vIPO), including a catalytically inactive vIPO.

12 Claims, 2 Drawing Sheets

(56) References Cited

OTHER PUBLICATIONS

Winter and Moore, "Exploring the chemistry and biology of vanadium-dependent haloperoxidases," *J. Biol. Chem.*, 284:18577-18581, 2009.

Xia et al., "Colorimetric detection of DNA, small molecules, proteins, and ions using unmodified gold nanoparticles and conjugated polyelectrolytes," *Proc. Natl. Acad. Sci. USA*, 107:10837-10841, 2010.

Zuo et al., "High specificity, electrochemical sandwich assays based on single aptamer sequences and suitable for the direct detection of small-molecule targets in blood and other complex matrices," *J. Am. Chem. Soc.*, 131:6944-6950, 2009.

Genbank Accession No. CAF04025.1, accessed Jan. 31, 2009.
Genbank Accession No. AJ619804.1, accessed Jan. 31, 2009.
Genbank Accession No. CAQ51446.1, accessed Jan. 31, 2009.
Genbank Accession No. AM992069.1, accessed Jan. 31, 2009.
Genbank Accession No. CQ871032.1, accessed Jan. 31, 2009.

\* cited by examiner

SEQUENCE LISTING

<160> NUMBER OF SEQ ID NOS: 5

<210> SEQ ID NO 1
<211> LENGTH: 624
<212> TYPE: PRT
<213> ORGANISM: Liminaria digitata

<400> SEQUENCE: 1

```
Met Lys Gly Leu Ala Gly Pro Ala Gly Ala Met Ala Val Val Ala Leu
1               5                   10                  15

Gly Leu Val Pro Gly Gly Ala Ile Gly Lys Ser Leu Arg Gln Glu Pro
            20                  25                  30

Ser Glu Pro Arg Leu Ser Gly Gly Val Asp Thr Ala Ala Ser Pro Ser
        35                  40                  45

Lys Asp Thr Leu Lys Gly Ser Leu Ser Arg Lys Leu Gln Val Val Asn
    50                  55                  60

Asp Asp Ala Leu Asp Val Ser Gly Thr Pro Ala Glu Arg Ala Ala Asn
65                  70                  75                  80

Ala Leu Asn Gln Arg Ile Glu Phe Ala Glu Thr Glu Phe Thr Ala Ser
                85                  90                  95

Glu Gly Thr Leu His Leu Asn Asn Gly Asp Arg Ser Ser Ala Ala Thr
            100                 105                 110

Phe His Lys Ser Leu Pro His Asp Ser Leu Gly Gln Val Asn Ser Glu
        115                 120                 125

Asp Phe Asp Leu Leu Met Glu Cys Ile Ala Gln Gly Asp Phe Asp Thr
    130                 135                 140

Cys Glu Leu Val Pro Ala Gly Asp Asp Gly Arg Leu Ser Asn Pro Leu
145                 150                 155                 160

Gly Gly Ile Ala Val Glu Met Ala Gly Ala Ala Gly Pro Ala Leu Thr
                165                 170                 175

Leu Pro Pro Ala Ser Ala Ile Asn Ser Glu Asp Leu Ala Ala Gln Met
            180                 185                 190

Ala Glu Gln Tyr Trp Met Ala Leu Thr Arg Asp Val Pro Phe Ser Gln
        195                 200                 205

Tyr Gly Glu Asp Glu Ala Thr Val Ala Ala Asp Asn Leu Ala Thr
    210                 215                 220

Met Pro Gly Phe Ala Asp Ile Val Gly Val Ala Val Asp Pro Glu Thr
225                 230                 235                 240

Arg Arg Ala Asp Pro Gln Ser Gln Leu Phe Arg Ser Ser Ala Phe Gly
                245                 250                 255
```

Val Glu Thr Gly Pro Phe Ile Ser Gln Leu Leu Val Lys Asp Phe Thr
            260                 265                 270

Ile Asp Ser Ile Thr Val Thr Pro Met Gln Lys Thr Phe Ala Pro Gly
        275                 280                 285

Ala Asp Tyr Met Thr Asp Tyr Asp Glu Trp Leu Ser Ile Gln Asn Gly
    290                 295                 300

Gly Ser Pro Asp Ser Glu Ala Asp Leu Asp Asp Glu Asp Arg Tyr Ile
305                 310                 315                 320

Arg Asn Ser Arg Asp Leu Ser Arg Leu Val Ala Thr Asp Thr Val Asn
                325                 330                 335

Thr Glu Ala Tyr Arg Ala Ala Leu Ile Leu Leu Asp Pro Asp Gln Gly
            340                 345                 350

Ala Asp Gly Arg Ala Ala Ile Ser Ala Pro Gly Leu Asn Gly Pro Tyr
        355                 360                 365

Ala Asp Ser Ser Arg Gln Ala Gly Phe Val Asn Tyr Gly Val Ser His
    370                 375                 380

Leu Met Arg Leu Val Gly Thr Ala Glu Leu Ala Gln Lys Ser Ala Trp
385                 390                 395                 400

Tyr Gln Lys Trp Asn Val His Met Phe Val Arg Pro Glu Ala Phe Gly
                405                 410                 415

Gly Ser Ile His Asn Val Leu Leu Gly Lys Leu Asp Val Glu Ile Ala
            420                 425                 430

Pro Ser Leu Leu Lys Asn Thr Asp Leu Leu Asp Arg Val Ala Ala Arg
        435                 440                 445

Asn Gly Glu Ile Asn Gly Arg Pro Gly Val Leu Asp Arg Thr Tyr Leu
    450                 455                 460

Leu Ser Gln Ala Leu Pro Glu Gly Ser Pro Thr His Pro Ser Tyr Pro
465                 470                 475                 480

Ala Gly His Ala Thr Gln Asn Gly Ala Phe Ala Thr Val Leu Lys Ala
                485                 490                 495

Leu Val Gly Leu Glu Arg Gly Ser Val Cys Phe Asn Asp Pro Val Phe
            500                 505                 510

Pro Asp Asp Glu Gly Leu Thr Leu Leu Pro Tyr Thr Gly Asp Asp Gly
        515                 520                 525

Asn Asn Cys Leu Thr Phe Glu Gly Glu Ile Asn Lys Leu Ala Val Asn
    530                 535                 540

Val Ala Leu Gly Arg Asn Met Leu Gly Val His Trp Arg Ile Asp Ser
545                 550                 555                 560

Glu Leu Gly Leu Leu Leu Gly Glu Thr Ala Ala Val Arg Ile Leu Gln
                565                 570                 575

Gln Glu Ala Val Ala Tyr Pro Glu Asn Ala Gly Tyr Glu Phe Arg Leu
            580                 585                 590

Met Ser Gly Lys Thr Ile Arg Leu Glu Thr Asp Gly Thr Phe Phe Ile
        595                 600                 605

Asp Asp Thr Leu Cys Ser Gly Asp Ala Phe Met Gly Ala Asp Leu Cys
    610                 615                 620

<210> SEQ ID NO 2
<211> LENGTH: 3733
<212> TYPE: DNA
<213> ORGANISM: Liminaria digitata

<400> SEQUENCE: 2
agaaaaagca ccgcctactg ctgccacgcc agaggaggac accatacact gtacttcctg    60

```
ttctgcatgc tgtaccgcgc ataggaatat catctgacca gcgtgcccat aaaaaaaggt    120
cgacatcgac tcgcaacatg aaggggcttg caggaccagc cggtgctatg gccgttgtcg    180
cgctcgggct tgtccccggc ggagcaatcg ggaaatcttt gcgacaagag ccctctgaac    240
cccgcctaag tggcggcgtg gatacggctg catcgccatc gaaggacacc ctgaaaggga    300
gtctttcgcg taagctccaa gtcgtcaacg atgatgccct cgatgttagt ggcacgcccg    360
cagaaagagc tgccaacgcg ctgaaccagc ggatcgaatt tgcggagacg gagttcacgg    420
catccgaagg cacgctccac cttaacaacg gagaccgctc atccgccgcc acgttccaca    480
agtcgctgcc gcacgacagc ctaggacagg tgaacagcga ggactttgac ctcctcatgg    540
agtgcatcgc tcaaggtgat ttcgacacat gcgagctggt gccggccgga gacgacggca    600
ggctgtccaa ccccctcggg ggtatcgccg tcgagatggc gggagccgcc ggccccgctt    660
tgaccctccc tccggcctca gcgatcaact ccgaggactt ggctgctcaa atggcggaac    720
agtactggat ggccttgacc agggacgtac ctttctctca gtacggcgag gatgaggcga    780
cagtggctgc agcagacaac ttggccacca tgcctggttt tgccgacatt gtcggggtgg    840
ccgtcgatcc ggaaaccaga agagcggatc cgcagtcgca gcttttccgg tcctctgcct    900
tcggcgtcga gacagggccc ttcatttccc agctactggt gaaggacttc acgattgatt    960
ctatcactgt gacgcctatg cagaagacgt ttgcgcccgg agcagactac atgaccgact   1020
acgacgaatg gctctccata cagaacggtg gcagccctga ctcggaagcg gacctagacg   1080
acgaggaccg gtacatccgc aactcccgcg acctctctag gctggtggct accgacaccg   1140
tcaacacgga ggcgtaccga gccgctctga ttcttctcga cccggaccag ggagccgatg   1200
gccgggcagc catcagcgct cccggcttga acggtcccta gcggacagc agccgccagg   1260
ccggcttcgt caactacggc gtgtctcacc ttatgaggct cgtcggaacc gccgagctgg   1320
cccagaagtc cgcgtggtac caaaagtgga acgtgcacat gttcgtacgt ccggaggctt   1380
tcggcggaag catccacaac gtcctcttgg gcaaactcga cgtagagatc gccccctcgc   1440
ttctcaaaaa cacggatttg ctagacaggg tggctgcacg gaacgggaa atcaacgggc    1500
ggccaggagt actcgaccgc acctacctcc tctcccaggc cctccccgag gggtcgccaa   1560
ctcacccatc gtaccccgct gggcacgcca cccagaacgg tgcattcgcc acggtgctca   1620
aggccctggt cgggctggag cgtggctctg tctgcttcaa tgacccgtg ttccccgacg    1680
acgaagggct gaccccttctg ccctacaccg gagacgacgg aaacaactgc ctaacattcg   1740
agggagaaat caacaagctg gccgtcaacg tggcattggg caggaacatg ttgggtgttc   1800
actggaggat cgacagcgag ttgggttgc ctcggcga acggcagct gtgaggatcc      1860
tgcagcagga ggccgtggca tacccagaga acgcgggata cgagttccgt ctgatgtcag   1920
gcaagaccat caggctcgaa accgacggga cattcttcat cgacgacacg ctgtgcagcg   1980
gggacgcgtt catgggagct gacctgtgct aatacgtcac acaagtgcca aggatctcgc   2040
tgctccacta gaaccgttta tgcggcggac gtggcccgat cgtaaaggca gtatcatatc   2100
gattgaacgt gcgctgggtt tcagcggcta ctactatgtc aacagtaaac ttgtaaaatt   2160
ggtcttcata aacagggcag tgttagatcg acgactggaa acgccagagg attgaagatc   2220
aacccaggta ttgctgaaaa agagtttcgc agcagtgatc tcttttgtta cggctatttc   2280
acatttgata catacatcgc ccgtttcaag acctacgctg tacaaacaac tatagctaga   2340
agtgttcagc gggcaacgtc ggcaaagtat cggccttcag cggtgacgg ctgtggggac    2400
tctgtttgga ccacacgttt attaatctgt tgacgtggaa gggaaagcct gcgtatccct   2460
```

-continued

```
aaggggcgca gcggggcgg tgatggttgg agtatcgatg ctaagcgtcc tatttatttg   2520
tgcaagtaag tggttgttgt tttggtaaat acggtggact cgagcgcgag gtatgtgctg   2580
gggagcaagc caccgtctac ggcatgtttg agacacccac cctgggcggc agcagaggtc   2640
gtaaggtccc agacgtgtca aacgggtgg gttttaagcg aatcgctgtt aggacggcat    2700
gcggtagctt cggcgggcct atctctgccc gccgcagagt acggcgtgat cgaattggct   2760
cgttctcggg tggcgagcat ggctatctac tgtagagtta gggttaggag catgaatggt   2820
acattacact ggtgttttgt tgtatgtgtt aagaacaaca gtctcagtac ctgtatcact   2880
actaaccacg tcggtgtctg gaaatattgc cttccaactt tccttctgct acaagatatt   2940
taattttaac tgtaggcata tgcacacttg gccatttgta agtgcgtgtt tcgtcttatg   3000
tgtaaggtgt agaaggtaca tctcttcatt aacatttgta attataaccg tacacacagc   3060
acagccagct tcttgctggt cttttcacgc gaagtcgcaa acagtttcg tcgatattcc    3120 gtcgttcatg gtcgtggaaa gattgcctgt aagtactttg catttcttcc ttcttgattc   3180
atgcacggcc gtgcatgacg ctatcgtttg cttcccttgg aaaatttggc gtgttatccg   3240
aagtagatca gccataatag tctatacatg tagcccttt cgattgaatc gacgacccgg    3300
tcttttgtgt gtatgagtgc ctcttggccg cggttttgag ctcctcaagt gaggaactac   3360
cggtttgtgt gagaatttca ctatgaatag tagaattagt tttgggacta ttaatagcgc   3420
atataaatgt tggtctgttc gtgcgatcga aatttgctcg aagtcatgtt tcgggggaaa   3480
ttttgagctc ctcaagtgag gagctcagaa cattctgctg cacccctata cccttgagat   3540
tactctcgat aaatcacagt agtctcgtgg ttttttcgag tttccaacaa attggtttcg   3600
cagtgcgact agtctcgcgg ttttttttat tttccaacaa attggtttcg cagggcgaca   3660
ccgttgaagg ttctgccaaa cacgtttgtt taccgtcatc ggcaattaaa taataacaac   3720
ggggttgatc ctg                                                      3733
```

<210> SEQ ID NO 3
<211> LENGTH: 613
<212> TYPE: PRT
<213> ORGANISM: Liminaria digitata

<400> SEQUENCE: 3

```
Met Lys Gly Leu Ala Gly Pro Ala Gly Ala Met Val Val Ala Leu
1               5                   10                  15

Gly Leu Val Pro Gly Gly Ala Ile Gly Lys Ser Leu Arg Gln Glu Pro
                20                  25                  30

Ser Glu Pro Arg Leu Ser Gly Gly Val Asp Thr Ala Val Ser Pro Ser
            35                  40                  45

Lys Asp Thr Leu Lys Gly Ser Leu Ser Arg Asn Leu Gln Val Ala Asn
        50                  55                  60

Asp Asp Ala Leu Asp Val Asn Gly Thr Pro Ala Glu Arg Ala Ala Asn
65                  70                  75                  80

Ala Leu Ala Gln Arg Ile Glu Leu Ala Glu Thr Glu Phe Ala Ala Ser
                85                  90                  95

Glu Gly Leu Phe His Val Asn Asn Gly Asp Arg Ser Ser Ala Ala Thr
            100                 105                 110

Phe His Lys Ser Leu Pro His Asp Ser Leu Gly Gln Val Asp Ser Ala
        115                 120                 125

Ala Phe Glu Ala Leu Thr Glu Cys Ile Ala Gln Gly Asp Phe Asp Ile
    130                 135                 140

Cys Glu Leu Val Pro Ala Gly Asp Val Gly Arg Leu Ser Asn Pro Leu
```

-continued

```
            145                 150                 155                 160
        Ala Gly Ile Thr Val Glu Met Ala Gly Ala Gly Ser Ala Leu Thr
                        165                 170                 175

Leu Pro Pro Ala Ser Ala Leu Asp Ser Glu Asp Leu Ala Ala Gln Met
                        180                 185                 190

Ala Glu Leu His Trp Met Ala Leu Thr Arg Asp Val Pro Phe Ser Gln
                        195                 200                 205

Tyr Gly Glu Asp Glu Ala Thr Val Ala Ala Asp Asn Leu Ala Thr
                210                 215                 220

Met Pro Gly Phe Gln Asn Met Val Gly Val Ala Val Asp Arg Asp Gly
        225                 230                 235                 240

Arg Ala Asp Pro Gln Ser Gln Leu Phe Arg Thr Ser Ala Phe Gly Val
                        245                 250                 255

Glu Thr Gly Pro Phe Ile Ser Gln Leu Leu Val Gln Asp Phe Thr Ile
                        260                 265                 270

Asp Ser Ile Thr Val Ala Pro Ile Gln Lys Thr Phe Glu Pro Gly Ala
                        275                 280                 285

Asp Tyr Met Ala Asp Tyr Asp Glu Trp Leu Phe Ile Gln Asn Gly Gly
                        290                 295                 300

Val Pro Asp His Asp Asp Val Leu Phe Asp Asp Val Asn Arg Tyr Ile
        305                 310                 315                 320

Arg Asn Ser Arg Asp Leu Ser Arg Leu Val Ala Ala Asp Thr Val Asn
                        325                 330                 335

Thr Glu Ala Tyr Arg Ala Ala Leu Ile Leu Leu Glu Gln Gly Ala Ile
                        340                 345                 350

Ser Gly Pro Gly Ser Asn Gly Pro Tyr Ala Gly Ser Ser Arg Gln Ala
                        355                 360                 365

Gly Phe Val Asn Tyr Gly Val Ser His Leu Met Arg Leu Val Gly Thr
                        370                 375                 380

Ala Glu Leu Ser Gln Lys Ser Ala Trp Tyr Gln Lys Trp Asn Val His
        385                 390                 395                 400

Met Phe Val Arg Pro Glu Ala Phe Gly Gly Thr Ile His Asn Val Leu
                        405                 410                 415

Leu Gly Lys Leu Asn Val Asp Ile Asn Pro Ser Leu Leu Lys Asn Thr
                        420                 425                 430

Glu Leu Leu Glu Arg Val Ala Glu Arg Asn Gly Val Ile Asn Gly Arg
                        435                 440                 445

Pro Gly Val Leu Asp Arg Thr Tyr Leu Leu Ser Gln Ala Val Ile Glu
                        450                 455                 460

Gly Ser Pro Thr His Pro Ser Tyr Pro Ala Gly His Ala Thr Gln Asn
        465                 470                 475                 480

Gly Ala Phe Ala Thr Val Leu Lys Ala Leu Val Gly Leu Glu Arg Gly
                        485                 490                 495

Ser Asp Cys Phe Arg Asp Pro Lys Val Pro Asp Glu Gly Leu Thr
                        500                 505                 510

Leu Leu Asp Phe Thr Gly Asp Cys Leu Thr Phe Glu Gly Glu Ile Asn
                        515                 520                 525

Lys Leu Ala Val Asn Val Ala Phe Gly Arg Asn Met Cys Gly Val His
                        530                 535                 540

Trp Arg Ile Asp Ser Glu Gln Gly Leu Leu Leu Gly Glu Met Ala Ala
        545                 550                 555                 560

Val Arg Ile Leu Gln Gln Glu Ala Val Thr Phe Pro Glu Asn Ala Gly
                        565                 570                 575
```

-continued

```
Tyr Glu Phe Asn Leu Met Ser Gly Glu Thr Ile Arg Leu Glu Thr Asp
                580                 585                 590

Gly Thr Phe Phe Ile Asn Asp Arg Leu Cys Ser Gly Asp Ala Phe Met
            595                 600                 605

Gly Ala Asp Leu Cys
        610

<210> SEQ ID NO 4
<211> LENGTH: 2719
<212> TYPE: PRT
<213> ORGANISM: Liminaria digitata

<400> SEQUENCE: 4

Cys Gly Gly Ala Thr Gly Thr Ala Cys Cys Gly Cys Gly Cys Ala Thr
  1               5                  10                  15

Ala Gly Ala Ala Ala Thr Ala Thr Cys Ala Thr Cys Thr Gly Ala Cys
                 20                  25                  30

Cys Ala Gly Cys Gly Thr Gly Cys Cys Ala Thr Ala Ala Ala Ala
             35                  40                  45

Ala Ala Ala Gly Gly Thr Cys Gly Ala Cys Ala Thr Cys Gly Ala Cys
         50                  55                  60

Thr Cys Gly Cys Ala Ala Cys Ala Thr Gly Ala Ala Gly Gly Gly
 65                  70                  75                  80

Cys Thr Thr Gly Cys Ala Gly Gly Ala Cys Cys Ala Gly Cys Cys Gly
                 85                  90                  95

Gly Thr Gly Cys Thr Ala Thr Gly Gly Thr Cys Gly Thr Thr Gly Thr
                100                 105                 110

Cys Gly Cys Gly Cys Thr Cys Gly Gly Gly Cys Thr Thr Gly Thr Cys
                115                 120                 125

Cys Cys Cys Gly Gly Cys Gly Gly Ala Gly Cys Ala Ala Thr Cys Gly
                130                 135                 140

Gly Gly Ala Ala Ala Thr Cys Thr Thr Thr Gly Cys Gly Ala Cys Ala
145                 150                 155                 160

Ala Gly Ala Gly Cys Cys Cys Thr Cys Thr Gly Ala Ala Cys Cys Cys
                165                 170                 175

Cys Gly Cys Cys Thr Cys Ala Gly Thr Gly Gly Cys Gly Gly Cys Gly
                180                 185                 190

Thr Gly Gly Ala Thr Ala Cys Gly Gly Cys Thr Gly Ala Thr Cys
                195                 200                 205

Gly Cys Cys Ala Thr Cys Gly Ala Ala Gly Gly Ala Cys Ala Cys Cys
                210                 215                 220

Cys Thr Gly Ala Ala Ala Gly Gly Gly Ala Gly Thr Cys Thr Thr Thr
225                 230                 235                 240

Cys Gly Cys Gly Thr Ala Ala Thr Cys Thr Thr Cys Ala Ala Gly Thr
                245                 250                 255

Cys Gly Cys Cys Ala Ala Cys Gly Ala Thr Gly Ala Thr Gly Cys Cys
                260                 265                 270

Cys Thr Cys Gly Ala Thr Gly Thr Thr Ala Ala Thr Gly Gly Cys Ala
                275                 280                 285

Cys Gly Cys Cys Cys Gly Cys Ala Gly Ala Ala Gly Ala Gly Cys
                290                 295                 300

Thr Gly Cys Cys Ala Ala Cys Gly Cys Gly Cys Thr Gly Cys Cys
305                 310                 315                 320

Cys Ala Gly Cys Gly Gly Ala Thr Cys Gly Ala Ala Thr Gly Gly
                325                 330                 335
```

-continued

Cys Gly Gly Ala Gly Ala Cys Gly Gly Ala Gly Thr Thr Cys Gly Cys
340 345 350

Gly Gly Cys Ala Thr Cys Cys Gly Ala Ala Gly Gly Cys Thr Thr Gly
355 360 365

Thr Thr Cys Cys Ala Cys Gly Thr Cys Ala Ala Cys Ala Ala Cys Gly
370 375 380

Gly Ala Gly Ala Cys Cys Gly Cys Thr Cys Ala Thr Cys Cys Gly Cys
385 390 395 400

Cys Gly Cys Cys Ala Cys Gly Thr Thr Cys Cys Ala Cys Ala Ala Gly
405 410 415

Thr Cys Gly Cys Thr Gly Cys Cys Gly Cys Ala Cys Gly Ala Cys Ala
420 425 430

Gly Cys Cys Thr Ala Gly Gly Ala Cys Ala Gly Gly Thr Gly Gly Ala
435 440 445

Cys Ala Gly Cys Gly Cys Gly Gly Cys Cys Thr Thr Thr Gly Ala Ala
450 455 460

Gly Cys Cys Cys Thr Cys Ala Cys Ala Gly Ala Gly Thr Gly Cys Ala
465 470 475 480

Thr Cys Gly Cys Thr Cys Ala Ala Gly Gly Thr Gly Ala Thr Thr Thr
485 490 495

Cys Gly Ala Cys Ala Thr Ala Thr Gly Cys Gly Ala Gly Cys Thr Gly
500 505 510

Gly Thr Gly Cys Cys Gly Gly Cys Cys Gly Gly Ala Gly Ala Cys Gly
515 520 525

Thr Thr Gly Gly Cys Ala Gly Gly Cys Thr Gly Thr Cys Cys Ala Ala
530 535 540

Cys Cys Cys Cys Cys Thr Cys Gly Cys Gly Gly Gly Thr Ala Thr Cys
545 550 555 560

Ala Cys Cys Gly Thr Cys Gly Ala Gly Ala Thr Gly Gly Cys Cys Gly
565 570 575

Gly Ala Gly Cys Cys Gly Cys Cys Gly Gly Cys Thr Cys Cys Gly Cys
580 585 590

Cys Thr Thr Gly Ala Cys Cys Cys Thr Cys Cys Cys Thr Cys Cys Gly
595 600 605

Gly Cys Cys Thr Cys Ala Gly Cys Gly Cys Thr Cys Gly Ala Cys Thr
610 615 620

Cys Cys Gly Ala Gly Gly Ala Cys Thr Thr Gly Gly Cys Thr Gly Cys
625 630 635 640

Thr Cys Ala Ala Ala Thr Gly Gly Cys Ala Gly Ala Ala Cys Thr Gly
645 650 655

Cys Ala Cys Thr Gly Gly Ala Thr Gly Gly Cys Cys Thr Thr Gly Ala
660 665 670

Cys Cys Ala Gly Gly Gly Ala Cys Gly Thr Ala Cys Cys Thr Thr Thr
675 680 685

Cys Thr Cys Thr Cys Ala Gly Thr Ala Cys Gly Gly Cys Gly Ala Ala
690 695 700

Gly Ala Thr Gly Ala Gly Gly Cys Gly Ala Cys Thr Gly Thr Gly Gly
705 710 715 720

Cys Thr Gly Cys Ala Gly Cys Ala Gly Ala Cys Ala Ala Cys Thr Thr
725 730 735

Gly Gly Cys Cys Ala Cys Cys Ala Thr Gly Cys Cys Thr Gly Gly Thr
740 745 750

Thr Thr Thr Cys Ala Ala Ala Ala Cys Ala Thr Gly Gly Thr Cys Gly
755 760 765

```
Gly Gly Gly Thr Gly Gly Cys Cys Gly Thr Cys Gly Ala Thr Cys Gly
        770             775             780
Gly Gly Ala Thr Gly Gly Cys Ala Gly Cys Gly Gly Ala Thr
785             790             795             800
Cys Cys Gly Cys Ala Gly Thr Cys Gly Cys Ala Gly Cys Thr Thr Thr
                805             810             815
Thr Cys Cys Gly Gly Ala Cys Cys Thr Cys Thr Gly Cys Cys Thr Thr
            820             825             830
Cys Gly Gly Cys Gly Thr Cys Gly Ala Gly Ala Cys Ala Gly Gly Gly
    835             840             845
Cys Cys Cys Thr Thr Cys Ala Thr Cys Thr Cys Cys Ala Gly Cys
    850             855             860
Thr Ala Cys Thr Gly Gly Thr Cys Ala Gly Gly Ala Cys Thr Thr
865             870             875             880
Cys Ala Cys Gly Ala Thr Thr Gly Ala Thr Cys Cys Ala Thr Cys
        885             890             895
Ala Cys Thr Gly Thr Gly Gly Cys Gly Cys Cys Thr Ala Thr Cys Cys
            900             905             910
Ala Gly Ala Ala Gly Ala Cys Gly Thr Thr Gly Ala Ala Cys Cys
        915             920             925
Cys Gly Gly Ala Gly Cys Ala Gly Ala Cys Thr Ala Cys Ala Thr Gly
    930             935             940
Gly Cys Cys Gly Ala Cys Thr Ala Cys Gly Ala Cys Gly Ala Ala Thr
945             950             955             960
Gly Gly Cys Thr Cys Thr Thr Cys Ala Thr Ala Cys Ala Gly Ala Ala
            965             970             975
Cys Gly Gly Thr Gly Gly Cys Gly Thr Gly Cys Cys Thr Gly Ala Cys
        980             985             990
Cys Ala Thr Gly Ala Cys Gly Ala  Thr Gly Thr Gly Cys  Thr Cys Thr
            995             1000            1005
Thr Thr  Gly Ala Cys Gly Ala  Cys Gly Thr Gly Ala  Ala Cys Cys
    1010            1015            1020
Gly Gly  Thr Ala Cys Ala Thr  Cys Cys Gly Cys Ala  Ala Cys Thr
    1025            1030            1035
Cys Cys  Cys Gly Cys Gly Ala  Cys Cys Thr Cys Thr  Cys Thr Ala
    1040            1045            1050
Gly Gly  Cys Thr Gly Gly Thr  Gly Gly Cys Thr Gly  Cys Cys Gly
    1055            1060            1065
Ala Cys  Ala Cys Cys Gly Thr  Cys Ala Ala Cys Ala  Cys Gly Gly
    1070            1075            1080
Ala Gly  Gly Cys Gly Thr Ala  Cys Cys Gly Ala Gly  Cys Cys Gly
    1085            1090            1095
Cys Thr  Cys Thr Gly Ala Thr  Thr Cys Thr Thr Cys  Thr Cys Gly
    1100            1105            1110
Ala Gly  Cys Ala Gly Gly Gly  Ala Gly Cys Cys Ala  Thr Cys Ala
    1115            1120            1125
Gly Cys  Gly Gly Thr Cys Cys  Cys Gly Gly Cys Thr  Cys Cys Ala
    1130            1135            1140
Ala Cys  Gly Gly Thr Cys Cys  Thr Ala Cys Gly Cys  Gly Gly
    1145            1150            1155
Gly Cys  Ala Gly Cys Ala Gly  Cys Cys Gly Cys Cys  Ala Gly Gly
    1160            1165            1170
Cys Cys  Gly Gly Cys Thr Thr  Cys Gly Thr Cys Ala  Ala Cys Thr
```

```
    1175                1180                1185

Ala Cys  Gly Gly Cys Gly Thr  Gly Thr Cys Cys Cys  Ala Cys Cys
    1190                1195                1200

Thr Thr  Ala Thr Gly Ala Gly  Gly Cys Thr Cys Gly  Thr Cys Gly
    1205                1210                1215

Gly Ala  Ala Cys Cys Gly Cys  Cys Gly Ala Gly Cys  Thr Gly Thr
    1220                1225                1230

Cys Cys  Cys Ala Gly Ala Ala  Gly Thr Cys Cys Gly  Cys Gly Thr
    1235                1240                1245

Gly Gly  Thr Ala Cys Cys Ala  Gly Ala Ala Gly Thr  Gly Gly Ala
    1250                1255                1260

Ala Cys  Gly Thr Gly Cys Ala  Cys Ala Thr Gly Thr  Thr Cys Gly
    1265                1270                1275

Thr Ala  Cys Gly Thr Cys Cys  Gly Gly Ala Gly Gly  Cys Thr Thr
    1280                1285                1290

Thr Cys  Gly Gly Cys Gly Gly  Ala Ala Cys Cys Ala  Thr Cys Cys
    1295                1300                1305

Ala Cys  Ala Ala Thr Gly Thr  Cys Cys Thr Cys Thr  Thr Gly Gly
    1310                1315                1320

Gly Cys  Ala Ala Ala Cys Thr  Cys Ala Ala Cys Gly  Thr Ala Gly
    1325                1330                1335

Ala Cys  Ala Thr Ala Ala Ala  Cys Cys Cys Cys Thr  Cys Gly Cys
    1340                1345                1350

Thr Thr  Cys Thr Cys Ala Ala  Ala Ala Ala Cys Ala  Cys Gly Gly
    1355                1360                1365

Ala Gly  Thr Thr Gly Cys Thr  Ala Gly Ala Gly Ala  Gly Gly Gly
    1370                1375                1380

Thr Gly  Gly Cys Thr Gly Ala  Ala Cys Gly Gly Ala  Ala Cys Gly
    1385                1390                1395

Gly Gly  Gly Thr Ala Ala Thr  Cys Ala Ala Cys Gly  Gly Gly Cys
    1400                1405                1410

Gly Gly  Cys Cys Ala Gly Gly  Ala Gly Thr Ala Cys  Thr Cys Gly
    1415                1420                1425

Ala Cys  Cys Gly Cys Ala Cys  Cys Thr Ala Cys Cys  Thr Cys Cys
    1430                1435                1440

Thr Cys  Thr Cys Cys Cys Ala  Gly Gly Cys Cys Gly  Thr Cys Ala
    1445                1450                1455

Thr Cys  Gly Ala Gly Gly Gly  Gly Thr Cys Gly Cys  Cys Ala Ala
    1460                1465                1470

Cys Thr  Cys Ala Cys Cys Cys  Ala Thr Cys Gly Thr  Ala Cys Cys
    1475                1480                1485

Cys Cys  Gly Cys Thr Gly Gly  Gly Cys Ala Cys Gly  Cys Cys Ala
    1490                1495                1500

Cys Cys  Cys Ala Gly Ala Ala  Cys Gly Gly Thr Gly  Cys Ala Thr
    1505                1510                1515

Thr Cys  Gly Cys Cys Ala Cys  Gly Gly Thr Gly Cys  Thr Cys Ala
    1520                1525                1530

Ala Gly  Gly Cys Cys Cys Thr  Gly Gly Thr Cys Gly  Gly Gly Cys
    1535                1540                1545

Thr Gly  Gly Ala Gly Cys Gly  Thr Gly Gly Cys Thr  Cys Thr Gly
    1550                1555                1560

Ala Cys  Thr Gly Cys Thr Thr  Cys Ala Gly Ala Gly  Ala Cys Cys
    1565                1570                1575
```

-continued

```
Cys Cys  Ala Ala Gly Gly Thr  Cys Cys Cys Cys Gly  Ala Cys Gly
    1580                 1585                 1590

Ala Cys  Gly Ala Ala Gly Gly  Gly Cys Thr Gly Ala  Cys Cys Cys
    1595                 1600                 1605

Thr Thr  Cys Thr Gly Gly Ala  Cys Thr Thr Cys Ala  Cys Cys Gly
    1610                 1615                 1620

Gly Gly  Gly Ala Cys Thr Gly  Cys Cys Thr Ala Ala  Cys Ala Thr
    1625                 1630                 1635

Thr Cys  Gly Ala Gly Gly Gly  Ala Gly Ala Ala Ala  Thr Cys Ala
    1640                 1645                 1650

Ala Cys  Ala Ala Gly Cys Thr  Gly Gly Cys Cys Gly  Thr Cys Ala
    1655                 1660                 1665

Ala Cys  Gly Thr Gly Gly Cys  Ala Thr Thr Cys Gly  Gly Cys Ala
    1670                 1675                 1680

Gly Gly  Ala Ala Cys Ala Thr  Gly Thr Gly Cys Gly  Gly Thr Gly
    1685                 1690                 1695

Thr Thr  Cys Ala Cys Thr Gly  Gly Ala Gly Gly Ala  Thr Cys Gly
    1700                 1705                 1710

Ala Cys  Ala Gly Cys Gly Ala  Gly Cys Ala Gly Gly  Gly Thr Thr
    1715                 1720                 1725

Thr Gly  Cys Thr Cys Cys Thr  Cys Gly Gly Cys Gly  Ala Gly Ala
    1730                 1735                 1740

Thr Gly  Gly Cys Ala Gly Cys  Thr Gly Thr Gly Ala  Gly Gly Ala
    1745                 1750                 1755

Thr Cys  Cys Thr Gly Cys Ala  Gly Cys Ala Gly Gly  Ala Gly Gly
    1760                 1765                 1770

Cys Cys  Gly Thr Gly Ala Cys  Ala Thr Thr Cys Cys  Cys Ala Gly
    1775                 1780                 1785

Ala Gly  Ala Ala Cys Gly Cys  Gly Gly Gly Ala Thr  Ala Cys Gly
    1790                 1795                 1800

Ala Gly  Thr Thr Cys Ala Ala  Thr Cys Thr Gly Ala  Thr Gly Thr
    1805                 1810                 1815

Cys Ala  Gly Gly Cys Gly Ala  Gly Ala Cys Cys Ala  Thr Cys Ala
    1820                 1825                 1830

Gly Gly  Cys Thr Cys Gly Ala  Ala Ala Cys Cys Gly  Ala Cys Gly
    1835                 1840                 1845

Gly Gly  Ala Cys Ala Thr Thr  Cys Thr Thr Cys Ala  Thr Cys Ala
    1850                 1855                 1860

Ala Cys  Gly Ala Cys Ala Gly  Gly Cys Thr Ala Thr  Gly Cys Ala
    1865                 1870                 1875

Gly Cys  Gly Gly Gly Gly Ala  Cys Gly Cys Gly Thr  Thr Cys Ala
    1880                 1885                 1890

Thr Gly  Gly Gly Ala Gly Cys  Thr Gly Ala Cys Cys  Thr Gly Thr
    1895                 1900                 1905

Gly Cys  Thr Ala Ala Thr Ala  Cys Gly Thr Cys Ala  Cys Ala Cys
    1910                 1915                 1920

Ala Ala  Ala Thr Gly Cys Cys  Ala Ala Gly Gly Ala  Thr Cys Gly
    1925                 1930                 1935

Cys Thr  Gly Cys Thr Cys Cys  Ala Cys Thr Ala Gly  Ala Ala Cys
    1940                 1945                 1950

Gly Gly  Thr Thr Thr Ala Thr  Gly Cys Gly Gly Cys  Gly Gly Ala
    1955                 1960                 1965

Cys Gly  Thr Gly Gly Cys Cys  Cys Gly Ala Thr Thr  Gly Thr Ala
    1970                 1975                 1980
```

-continued

```
Ala Ala Gly Gly Cys Ala Gly Thr Ala Thr Cys Ala Thr Ala Thr
    1985                1990                1995

Cys Cys Ala Cys Thr Gly Ala Ala Cys Gly Thr Gly Cys Gly Cys
    2000                2005                2010

Thr Gly Gly Gly Thr Thr Thr Cys Ala Gly Cys Gly Gly Cys Thr
    2015                2020                2025

Ala Cys Thr Ala Cys Gly Ala Thr Gly Thr Cys Ala Ala Cys Ala
    2030                2035                2040

Gly Thr Ala Ala Ala Cys Thr Thr Gly Thr Ala Ala Ala Ala Thr
    2045                2050                2055

Thr Gly Gly Thr Cys Thr Thr Cys Ala Thr Ala Ala Ala Cys Ala
    2060                2065                2070

Gly Gly Gly Thr Ala Gly Thr Gly Thr Thr Thr Gly Ala Thr Cys
    2075                2080                2085

Gly Ala Cys Gly Ala Cys Thr Gly Gly Ala Ala Ala Cys Gly Cys
    2090                2095                2100

Cys Ala Gly Ala Gly Gly Ala Thr Thr Gly Ala Ala Gly Ala Thr
    2105                2110                2115

Cys Ala Ala Cys Cys Cys Ala Gly Gly Thr Ala Thr Thr Gly Thr
    2120                2125                2130

Thr Gly Ala Ala Ala Thr Ala Thr Ala Gly Thr Thr Thr Cys Gly
    2135                2140                2145

Gly Ala Gly Cys Ala Gly Thr Gly Ala Thr Cys Thr Cys Thr Thr
    2150                2155                2160

Thr Thr Gly Thr Thr Ala Cys Gly Gly Cys Thr Ala Thr Thr Cys
    2165                2170                2175

Ala Thr Ala Cys Gly Thr Gly Cys Thr Ala Thr Ala Cys Ala Thr
    2180                2185                2190

Ala Cys Ala Thr Cys Gly Cys Cys Cys Gly Thr Thr Thr Cys Ala
    2195                2200                2205

Ala Gly Ala Cys Cys Thr Ala Cys Gly Cys Thr Ala Thr Ala Cys
    2210                2215                2220

Gly Ala Ala Cys Thr Ala Ala Gly Cys Thr Ala Gly Gly Ala Gly
    2225                2230                2235

Thr Gly Thr Thr Cys Ala Gly Cys Gly Gly Gly Cys Ala Ala Cys
    2240                2245                2250

Gly Thr Cys Gly Gly Cys Ala Ala Ala Thr Ala Thr Cys Gly Gly
    2255                2260                2265

Cys Cys Thr Cys Thr Ala Gly Cys Gly Gly Thr Gly Gly Ala Cys
    2270                2275                2280

Gly Thr Cys Thr Gly Thr Gly Gly Gly Gly Gly Cys Thr Cys Thr
    2285                2290                2295

Gly Thr Gly Gly Thr Thr Gly Gly Ala Cys Cys Ala Ala Ala Cys
    2300                2305                2310

Gly Thr Thr Thr Cys Ala Thr Cys Thr Thr Thr Cys Gly Ala Cys
    2315                2320                2325

Gly Thr Gly Gly Ala Ala Gly Gly Ala Ala Ala Ala Gly Cys Cys
    2330                2335                2340

Thr Gly Cys Gly Thr Ala Thr Cys Cys Cys Thr Ala Ala Gly Gly
    2345                2350                2355

Gly Gly Cys Gly Cys Ala Gly Cys Gly Gly Gly Gly Gly Cys Gly
    2360                2365                2370

Gly Ala Gly Ala Thr Gly Gly Thr Thr Gly Gly Ala Gly Thr Ala
```

2375                2380                2385

Thr Cys Gly Ala Gly Gly Cys Thr Ala Ala Gly Cys Gly Thr Cys
            2390                2395                2400

Ala Thr Thr Gly Thr Thr Ala Thr Thr Thr Gly Thr Gly Cys Ala
            2405                2410                2415

Ala Gly Thr Ala Cys Gly Thr Cys Gly Thr Thr Gly Thr Thr Gly
            2420                2425                2430

Thr Thr Thr Thr Gly Ala Thr Ala Ala Ala Gly Thr Gly Gly Ala
            2435                2440                2445

Cys Thr Cys Gly Ala Gly Cys Gly Cys Gly Ala Gly Gly Thr Ala
            2450                2455                2460

Thr Gly Thr Gly Cys Ala Gly Gly Thr Ala Thr Cys Ala Gly Thr
            2465                2470                2475

Cys Ala Gly Gly Cys Thr Gly Gly Gly Ala Gly Cys Ala Ala
            2480                2485                2490

Gly Cys Cys Ala Cys Cys Gly Thr Cys Thr Ala Cys Gly Gly Thr
            2495                2500                2505

Ala Thr Gly Thr Thr Thr Gly Ala Ala Ala Cys Ala Cys Cys Cys
            2510                2515                2520

Ala Cys Cys Cys Thr Gly Gly Gly Cys Gly Gly Cys Ala Gly Cys
            2525                2530                2535

Ala Gly Ala Gly Gly Thr Ala Gly Thr Ala Ala Gly Gly Thr Cys
            2540                2545                2550

Cys Cys Ala Ala Ala Cys Gly Thr Gly Thr Thr Ala Ala Gly Cys
            2555                2560                2565

Ala Thr Gly Thr Thr Gly Gly Cys Thr Thr Thr Ala Ala Gly
            2570                2575                2580

Cys Gly Ala Ala Thr Cys Gly Cys Thr Gly Thr Gly Thr Thr
            2585                2590                2595

Ala Gly Gly Ala Cys Gly Gly Cys Ala Thr Gly Gly Thr Thr
            2600                2605                2610

Ala Gly Cys Thr Thr Cys Gly Gly Cys Gly Gly Gly Cys Cys Thr
            2615                2620                2625

Ala Thr Cys Thr Cys Thr Gly Cys Cys Cys Gly Cys Gly Gly Cys
            2630                2635                2640

Ala Gly Ala Gly Thr Ala Thr Gly Gly Cys Gly Thr Gly Ala Thr
            2645                2650                2655

Gly Gly Ala Ala Thr Thr Gly Gly Cys Thr Cys Gly Thr Thr Cys
            2660                2665                2670

Thr Cys Gly Gly Gly Thr Gly Gly Cys Gly Ala Gly Cys Ala Thr
            2675                2680                2685

Gly Thr Cys Thr Ala Thr Cys Thr Ala Cys Thr Gly Thr Thr Ala
            2690                2695                2700

Ala Gly Ala Gly Gly Gly Ala Gly Thr Thr Ala Gly Gly Gly Cys
            2705                2710                2715

Thr

<210> SEQ ID NO 5
<211> LENGTH: 4313
<212> TYPE: DNA
<213> ORGANISM: Liminaria digitata

<400> SEQUENCE: 5
gacaacttgg ccaccatgcc tggttttgcc gacattgtcg ggtggccgt cgatccggaa    60

-continued

| | |
|---|---|
| accagaagag cggatccgca gtcgcagctt ttccggtcct ctgccttcgg cgtcgagaca | 120 |
| gggcccttca tttcccagct actggtgaag gacttcacga ttgattctat cactgtgacg | 180 |
| cctatgcaga agacgtttgc cccggagcag actacatgac cgactacgac gaatggctct | 240 |
| ccatacagaa cggtggcagc cctgactcgg aagcggacct agacgacgag gaccggtaca | 300 |
| tccgcaactc ccgcgaccct ctaggctgg tggctaccga caccgtcaac acggaggcgt | 360 |
| accgagccgc tctgattctt ctcgacccgg accagggagc cgatggccgg gcagccatca | 420 |
| gcgctcccgg cttgaacggt ccctacgcgg acagcagccg ccaggccggc ttcgtcaact | 480 |
| acggcgtgtc tcaccttatg aggctcgtcg aaccgccga gctggcccag aagtccgcgt | 540 |
| ggtaccaaaa gtggaacgtg cacatgttcg tacgtccgga ggctttcggc ggaagcatcc | 600 |
| acaacgtcct cttgggcaaa ctcgacgtag agatcgcccc ctcgcttctc aaaaacacgg | 660 |
| atttgctaga cagggtggct gcacggaacg gggaaatcaa cgggcggcca ggagtactcg | 720 |
| accgcaccta cctcctctcc caggccctcc ccgaggggtc gccaactcac ccatcgtacc | 780 |
| ccgctgggca cgccacccag aacggtgcat tcgccacggt gctcaaggcc ctggtcgggc | 840 |
| tggagcgtgg ctctgtctgc ttcaatgacc ccgtgttccc cgacgacgaa gggctgaccc | 900 |
| ttctgcccta caccggagac gacggaaaca actgcctaac attcgaggga gaaatcaaca | 960 |
| agctggccgt caacgtggca ttgggcagga acatgttggg tgttcactgg aggatcgaca | 1020 |
| gcgagttggg tttgctcctc ggcgagacgg cagctgtgag gatcctgcag caggaggccg | 1080 |
| tggcataccc agagaacgcg ggatacgagt tccgtctgat gtcaggcaag accatcaggc | 1140 |
| tcgaaaccga cgggacattc ttcatcgacg acacgctgtg cagcggggac gcgttcatgg | 1200 |
| gagctgacct gtgctaatac gtcacacaag tgccaaggat ctcgctgctc cactagaacc | 1260 |
| gtttatgcgg cggacgtggc ccgatcgtaa aggcagtatc atatcgattg aacgtgcgct | 1320 |
| gggtttcagc ggctactact atgtcaacag taaacttgta aaattggtct tcataaacag | 1380 |
| ggcagtgtta gatcgacgac tggaaacgcc agaggattga agatcaaccc aggtattgct | 1440 |
| gaaaaagagt ttcgcagcag tgatctcttt tgttacggct atttcacatt tgatacatac | 1500 |
| atcgcccgtt tcaagaccta cgctgtacaa acaactatag ctagaagtgt tcagcgggca | 1560 |
| acgtcggcaa agtatcggcc ttcagcggtg gacggctgtg gggactctgt ttggaccaca | 1620 |
| cgtttattaa tctgttgacg tggaagggaa agcctgcgta tccctaaggg gcgcagcggg | 1680 |
| ggcggtgatg gttggagtat cgatgctaag cgtcctattt atttgtgcaa gtaagtggtt | 1740 |
| gttgttttgg taaatacggt ggactcgagc gcgaggtatg tgctggggag caagccaccg | 1800 |
| tctacggcat gtttgagaca cccacccctgg gcggcagcag aggtcgtaag gtcccagacg | 1860 |
| tgtcaaacgg gttgggtttt aagcgaatcg ctgttaggac ggcatgcggt agcttcggcg | 1920 |
| ggcctatctc tgcccgccgc agagtacggc gtgatcgaat tggctcgttc tcgggtggcg | 1980 |
| agcatggcta tctactgtag agttagggtt aggagcatga atggtacatt acactggtgt | 2040 |
| tttgttgtat gtgttaagaa caacagtctc agtacctgta tcactactaa ccacgtcggt | 2100 |
| gtctggaaat attgccttcc aactttcctt ctgctacaag atatttaatt ttaactgtag | 2160 |
| gcatatgcac acttggccat ttgtaagtgc gtgtttcgtc ttatgtgtaa ggtgtagaag | 2220 |
| gtacatctct tcattaacat ttgtaattat aaccgtacac acagcacagc cagcttcttg | 2280 |
| ctggtctttt cacgcgaagt cgcaaaacag tttcgtcgat attccgtcgt tcatggtcgt | 2340 |
| ggaaagattg cctgtaagta cttttgcattt cttccttctt gattcatgca cggccgtgca | 2400 |
| tgacgctatc gtttgcttcc cttggaaaat ttggcgtgtt atccgaagta gatcagccat | 2460 |

-continued

```
aatagtctat acatgtagcc cttttcgatt gaatcgacga cccggtcttt tgtgtgtatg    2520
agtgcctctt ggccgcggtt ttgagctcct caagtgagga actaccggtt tgtgtgagaa    2580
tttcactatg aatagtagaa ttagttttgg gactattaat agcgcatata aatgttggtc    2640
tgttcgtgcg atcgaaattt gctcgaagtc atgtttcggg ggaaattttg agctcctcaa    2700
gtgaggagct cagaacattc tgctgcaccc ctatacccct gagattactc tcgataaatc    2760
acagtagtct cgtggttttt tcgagtttcc aacaaattgg tttcgcagtg cgactagtct    2820
cgcggttttt tttattttcc aacaaattgg tttcgcaggg cgacaccgtt gaaggttctg    2880
ccaaacacgt ttgtttaccg tcatcggcaa ttaaataata acaacggggt tgatcctgtc    2940
agctctgctt ggtcgtgata gtatatatta gtcggcagaa cgtccttcgt gccggctcgc    3000
gaacgaaggt tcccctgta gcacggcctt cttaacgcca acttttggaa catactaatg    3060
atatcgagac acgcgctaaa cgttctagac atgcacgtag ttgtccattt tgttgacatg    3120
caacagcact ggcctttggc cttgggtttt gtcattggca cattccgact gaataaacca    3180
acgaaaatgc gagcatccag tgtgcatcgc agaatacacg gcatccgcct aatcgttcac    3240
ctggtagtcg acacaaaaaa agagtgtcag caaaacgaca cgacctgttg catatcaata    3300
acctttctgt ggccttagta tgactttcac actgcaggta ggttgggctt tgtccccatt    3360
acactcgttt agactaccgc agtattgtgt atgggctgtt cttaccggag cgagagctag    3420
cacgacttgg gccccgacgc taccgtatcc ttctcgggaa tcgcccgtag cgacaagcat    3480
tcttgttaag agcttaccgt tctttcctc gaagcggcga gtttccttcg cgaactgcgt    3540
cctctgcagc cgagtggcat cctcctctaa ctctgcaggc gcagtctcta ggcccgacat    3600
gactttgccg aggccgtcct cgtacatcag cgaccgctgt aatgtaatcc aaccatgata    3660
ctggttgggt tctccaccga atggagagaa tccgtctcta aaaggagagg acatggttga    3720
ctctaaatcg acaccaccat gttgactcat aacttgacaa gactacagca gtatagcatg    3780
tagtattggc gtcgctgcac cacgtaatcg tgcagtagct agcgccgaac agaggttcgg    3840
gtagagcaaa aacagagtga cttaatatct cacagatcag gcgtcgaagc tgcctgatct    3900
gacggtttca tagcaaagtc aaccgccata caatacagta aaaaacccca atagcacatg    3960
gagttgatct tgcactacca atatcctgac agcaatccct cggtaggggt accatttttt    4020
ggctcaatag tttctgaccg tttgagcttc tcaagtgaga aactaacggt tagcttcata    4080
atttttaagt gtacttgttt ttgtttaggg ttccttgtca ttccacactc cccctgttc    4140
gtttggatca ttctagcaat gacggcttca tttagtagag gagttcccaa atattctctg    4200
acgttatgat ggattgttgc cggaggttgg agtttgggca tcgaggttct ctctcctctt    4260
ctcctcttct cctcttctgc tcttgctagg tgctctaata caacgatata aag           4313
```

POINT OF CARE IODINE SENSOR

CROSS REFERENCE TO RELATED APPLICATION

This application is a continuation of U.S. patent application Ser. No. 13/363,295, filed Jan. 31, 2012 now abandoned, which claims the benefit of U.S. Provisional Application 61/438,115, filed Jan. 31, 2011, both of which are incorporated herein by reference.

FIELD

The disclosure pertains to methods of detecting iodine status in a subject, and test devices for use in such methods.

BACKGROUND

Iodine is a micronutrient critical for normal human development and thyroid function. Iodine deficiency occurs in geographic areas that lack iodine in the soil and water as a result of geologic activity. Many such areas are found worldwide and approximately 30% of the world's population, in 130 countries across the globe, live in iodine deficient areas.

Health problems associated with deficient iodine intake are known collectively as iodine deficiency disorders (IDD). These disorders range from goiters and mild neurologic deficiencies to overt mental and physician retardation and cretinism. Iodine deficiency remains the leading cause of preventable mental retardation worldwide.

Preventing IDD is straightforward. Supplementing iodine intake into the diet of people living in areas of endemic iodine deficiency can successfully prevent IDD. Iodinization of salt is an inexpensive and commonly used method to increase iodine intake in a community. Despite the effectiveness and low cost of this intervention, millions remain at risk for IDD because they lack access to iodize salt, the available salt is inadequately iodized or they do not ingest the iodized salt. Therefore, periodic monitoring of the dietary iodine intake is important. Additional information concerning IDD can be found in the references cited below, all of which are incorporated herein by reference.

In view of the above, periodic testing and monitoring for iodine deficiency could be beneficial. The current standard for assessing iodine deficiency is measurement of urinary iodine. Measuring urine iodine is a standardized laboratory test, which utilizes the oxidative-reductive capacity of iodine, which subsequently catalyzes a color reaction. Although relatively simple to do in a laboratory, the testing is not conducive to rapid, individual point of care testing. Point of care iodine deficiency testing that is simple and permits individuals or small clinics to assess the iodine status at any time is required. If iodine status is determined to be low, communities and individuals will be motivated to take advantage of sources of iodine including iodized salt.

Iodine is stored in the thyroid, breast and salivary glands. Of these, the salivary glands are a useful source of material for detecting the iodine level in a subject given the ease of access to saliva, the inorganic form of iodine in saliva and because the release of iodine from the salivary gland is not affected by plasma iodine levels. However, attempts to quantitate iodide in salvia using iodide binding moieties have been problematic because the presence of other salivary halides interferes with the assay.

SUMMARY

Methods of detecting iodine status in a subject, and embodiments of a test device for use in such methods, are disclosed. The methods and devices can be used, for example, to detect iodine deficiency or iodine overabundance in a subject. The disclosed methods and devices utilize a protein that specifically binds to iodide, but not other halides in saliva, to detect iodide in saliva.

The methods include contacting a saliva sample from the subject with an effective amount of an iodide binding protein (IBP) that specifically binds to iodide under conditions sufficient for specific binding of the IBP to iodide. Iodide binding to the IBP is detected and compared with a control. Comparing the detected binding of iodide to the IBP with the control identifies the iodine status in the subject. For example, comparing the detected binding of iodide to the IBP with a control can include identifying the iodide concentration in the saliva sample, which can be used to identify the iodine status of the subject.

In several embodiments, the IBP includes a vanadium-dependent iodoperoxidase (vIPO), such as a catalytically inactive vIPO or a iodide binding domain of a vIPO. For example the IBP can include the polypeptide comprising an amino acid sequence set forth as amino acids 282-624 of SEQ ID NO: 1, wherein the IBP specifically binds to iodide. In some embodiments, the IBP includes an amino acid sequence having at least 90% sequence identity to SEQ ID NO: 1 or SEQ ID NO: 3, wherein the IBP specifically binds to iodide.

Detecting iodide binding to the IBP can include, for example, detecting surface plasmon resonance, FRET, gold nanoparticle aggregation and/or a detectable marker.

Embodiments of a test device for use in the provided methods are also disclosed. In some embodiments, the test device includes a sample receiving zone that can accept a saliva sample from a subject, and an iodide capture zone comprising an IBP that specifically binds to iodide. The sample receiving zone is coupled to the iodide capture zone and application of a liquid saliva sample to the sample receiving zone results in application of the liquid saliva sample to the iodide capture zone. Iodide in the saliva sample specifically binds to the IBP included in the iodide capture zone. The test device is configured such that iodide specifically bound to the IBP can be detected using methods disclosed herein.

The disclosed test devices and methods for detecting iodine deficiency in a subject promote on-going use of iodine supplements in regions of endemic iodine deficiency. The test devices and methods for identifying a subject with iodine deficiency do not need to quantitative, but instead a qualitative assessment of iodine stores can be used to identify iodine deficiency in a subject.

The foregoing and other objects, features, and advantages of the disclosed technologies will become more apparent from the following detailed description, which proceeds with reference to the accompanying figures.

SEQUENCE LISTING

Figure 1:
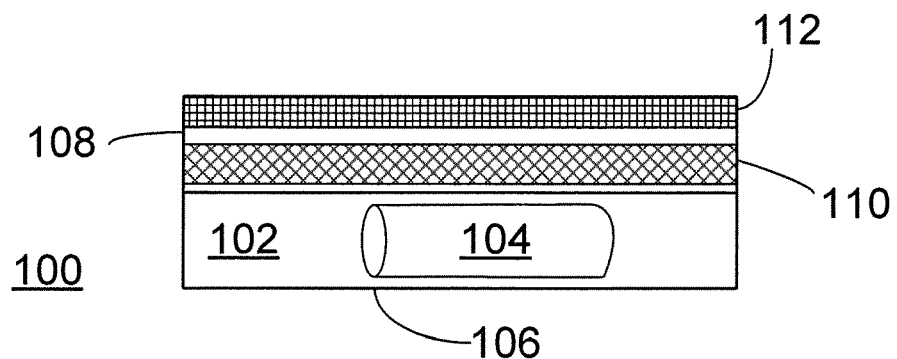
FIG. 1 is a schematic diagram of a representative IBP-based iodine sensor.

The nucleic and amino acid sequences provided herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt," which was created on Jan. 26, 2012, and is 44,400 bytes, which is incorporated by reference herein. In the accompanying sequence listing:

SEQ ID NO: 1 is the amino acid sequence of *Laminaria digitata* vanadium-dependent iodoperoxidase 1 (disclosed as SEQ ID NO: 3 in Int. Pat. App. Pub. No. WO2004/078976; Genbank Accession No. CAF04025.1).

SEQ ID NO: 2 is an exemplary nucleic acid sequence encoding *Laminaria digitata* vanadium-dependent iodoperoxidase 1 (disclosed as SEQ ID NO: 18 in Int. Pat. App. Pub. No. WO2004/078976; Genbank Accession No. AJ619804.1).

SEQ ID NO: 3 is the amino acid sequence of *Laminaria digitata* vanadium-dependent iodoperoxidase 3 (Genbank Accession No. CAQ51446.1).

SEQ ID NO: 4 is an exemplary nucleic acid sequence encoding *Laminaria digitata* vanadium-dependent iodoperoxidase 3 (Genbank Accession No. AM992069.1).

SEQ ID NO: 5 is an exemplary nucleic acid sequence encoding amino acids 282-624 of SEQ ID NO: 1 (disclosed as SEQ ID NO: 20 in Int. Pat. App. Pub. No. WO2004/078976; Genbank Accession No. CQ871032.1).

DETAILED DESCRIPTION

I. Abbreviations

| | |
|---|---|
| IBP | Iodide Binding Protein |
| vIPO | Vanadium Iodoperoxidase |
| IDD | Iodine Deficiency Disorder |
| SPR | Surface Plasmon Resonance |
| FRETF | Förster resonance energy transfer |

II. Terms

Unless otherwise noted, technical terms are used according to conventional usage. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Terms describing protein structure and structural elements of proteins can be found in Creighton, Proteins, Structures and Molecular Properties, W.H. Freeman & Co., New York, 1993 (ISBN 0-717-7030) which is incorporated by reference herein in its entirety.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise.

It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. All GENBANK® Accession numbers are herein incorporated by reference as they appear in the database on Jan. 27, 2012. In case of conflict, the present specification, including explanations of terms, will control. In addition, the materials, methods, and examples are illustrative only and not intended to be limiting.

To facilitate review of the various embodiments of this disclosure, the following explanations of terms are provided:

Antibody: "Antibody" collectively refers to immunoglobulins or immunoglobulin-like molecules (including by way of example and without limitation, IgA, IgD, IgE, IgG and IgM, combinations thereof, and similar molecules produced during an immune response in any chordate such as a vertebrate, for example, in mammals such as humans, goats, rabbits and mice) and fragments thereof that specifically bind to a molecule of interest (or a group of highly similar molecules of interest) to the substantial exclusion of binding to other molecules. An "antibody" typically comprises a polypeptide ligand having at least a light chain or heavy chain immunoglobulin variable region that specifically recognizes and binds an epitope of an antigen. Immunoglobulins are composed of a heavy and a light chain, each of which has a variable region, termed the variable heavy ($V_H$) region and the variable light ($V_L$) region. Together, the $V_H$ region and the $V_L$ region are responsible for binding the antigen recognized by the immunoglobulin. Exemplary immunoglobulin fragments include, without limitation, proteolytic immunoglobulin fragments (such as F(ab')$_2$ fragments, Fab' fragments, Fab'-SH fragments and Fab fragments as are known in the art), recombinant immunoglobulin fragments (such as sFv fragments, dsFv fragments, bispecific sFv fragments, bispecific dsFv fragments, F(ab)'$_2$ fragments, single chain Fv proteins ("scFv"), and disulfide stabilized Fv proteins ("dsFv")). Other examples of antibodies include diabodies, and triabodies (as are known in the art), and camelid antibodies. "Antibody" also includes genetically engineered molecules, such as chimeric antibodies (for example, humanized murine antibodies), and heteroconjugate antibodies (such as, bispecific antibodies). See also, Pierce Catalog and Handbook, 1994-1995 (Pierce Chemical Co., Rockford, Ill.); Kuby, *J., Immunology*, 3$^{rd}$ Ed., W.H. Freeman & Co., New York, 1997.

The antibodies disclosed herein specifically bind a defined target (or multiple targets, in the case of a bispecific antibody). It is, of course, recognized that a certain degree of non-specific interaction may occur between an antibody and a non-target.

A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Bibulous: absorbent. In some embodiments, test devices disclosed herein include a bibulous material, such as a porous matrix, in which liquid flows by capillary action though the matrix. Bibulous material is capable of supporting bibulous lateral flow and non-bibulous lateral flow. Non-bibulous lateral flow refers to liquid flow in which all of the dissolved or dispersed components of the liquid are carried at substantially equal rates and with relatively unimpaired flow, laterally through the membrane or matrix, as opposed to bibulous flow in which different components flow at different rates. In certain examples disclosed herein, different components of liquid flow separate into distinct wave fronts that reach capture zones sequentially instead of simultaneously. The degree of separation of wave fronts can be controlled using a variety of factors, such as the pore size of the bibulous matrix (larger components move more slowly through the pores), weight (heavier components flow more slowly), and interactions with the substrate (hydrophobic, charge or other interactions between a component and the matrix alter migration rate).

Bibulous materials, such as untreated paper, cellulose blends, nitrocellulose, polyester, acrylonitrile copolymers, rayon, glass fiber, and the like may also be employed as support matrix materials to provide non-bibulous flow. Especially preferred are microporous materials made from nitrocellulose, by which term is meant any nitric acid ester of cellulose. Thus suitable materials may include nitrocellulose in combination with carboxylic acid esters of cellulose. The pore size of nitrocellulose membranes may vary widely, but is preferably within 1 to 20 microns, preferably 8 to 15 microns. Bibulous flow can be enhanced by various methods that alter the binding properties of the support matrix, or by selectively placing different reagents in different support matrix environments, or positions on the strip that restrict or enhance flow. To provide non-bibulous flow, these materials may be treated with blocking agents that may block the forces which account for the bibulous nature of bibulous materials. Suitable blocking agents include bovine serum albumin (BSA), methylated bovine serum albumin, whole animal serum, casein, and non-fat dry milk. Certain localized regions of a test device may be blocked without completely abolishing differential flow on the test device.

Conjugate: A complex of two molecules coupled together, for example, linked together by a covalent bond or non-covalent interaction. The linkage can be by chemical or recombinant means, for example. In one example, a conjugate includes an antibody coupled to a peroxidase enzyme. In one embodiment, the linkage is chemical, wherein a reaction between an antibody and a peroxidase enzyme forms a covalent bond between the two molecules to form one molecule. A peptide linker (short peptide sequence) can optionally be included.

Conjugating, joining, bonding or linking: Coupling a first molecule to a second molecule. This includes, but is not limited to, covalently bonding one molecule to another molecule, noncovalently bonding one molecule to another molecule (e.g., electrostatically bonding) (see, for example, U.S. Pat. No. 6,921,496), hydrogen bonding, van der Waals forces, and any and all combinations of such couplings. For example, linking two polypeptides into one contiguous polypeptide, or covalently attaching an effector molecule or detectable marker radionuclide or other molecule to a polypeptide, such as an antibody.

Consists of: With regard to a polypeptide, a polypeptide that consists of a specified amino acid sequence does not include any additional amino acid residues, nor does it include additional non-peptide components, such as lipids, sugars or labels.

Contacting: Placement in direct association, for example solid, liquid or gaseous forms. Contacting includes, for example, direct association of fully- and partially-solvated molecules.

Control: A sample or standard used for comparison with a test sample, such as a biological sample, e.g., a saliva sample obtained from a subject (or plurality of subjects). In some embodiments, the control is a saliva sample obtained from a healthy subject (or plurality of subjects) (also referred to herein as a "normal" control). In some embodiments, the control is a historical control or standard value (i.e. a previously tested control sample or group of samples that represent baseline or normal values). In some embodiments the control is a standard value representing the average value (or average range of values) obtained from a plurality of subject samples.

Coupled: A first molecule or structure operably connected to a second molecule or structure. For example, a detectable marker can be coupled to a binding protein via a covalent bond for use in the methods of detecting the presence of the binding protein. Alternatively, a sample receiving zone of a test device can be coupled to a binding zone of the test device such that liquid sample applied to the sample receiving zone transits to the binding zone. For example, in some embodiments, the sample receiving zone can be coupled to the binding zone via a flexible capillary tube, or via a bibulous material capable of lateral flow from the sample receiving zone to the binding zone.

Detect or determine an analyte: An analyte (such as iodide) is "detected" when its presence is ascertained or discovered. "Determination" of an analyte (such as iodide) refers to detecting an amount/concentration (either approximate or exact) of the analyte. Hence "detection" is a generic term that includes either ascertaining its presence or determining an amount/concentration (since determining an amount also indicates the presence of the analyte). General methods of detecting and determining are known to the person of ordinary skill in the art and may be supplemented with the protocols and reagents disclosed herein. For example, included herein are methods of detecting iodide concentration in a saliva sample from a subject.

Detectable marker: A label capable of providing a signal that can indicate to an observer the presence of the label. A detectable marker may be, for example, any molecule or composition that is detectable by spectroscopic, photochemical, biochemical, immunochemical, electrical, visual (including optical) or chemical means. Examples of detectable markers include enzymes, heavy metals colloidal gold particles, carbon particles, colored latex particles, fluorescent molecules, and others such as those disclosed in U.S. Pat. Nos. 4,275,149, 4,313,734, 4,373,932, and 4,954,452, all of which are incorporated by reference herein to provide additional examples of detectable markers.

The attachment of a detectable marker to a target being labeled can be through covalent bonds, adsorption processes, hydrophobic and/or electrostatic bonds, as in chelates and the like, or combinations of these bonds and interactions and/or may involve a linking group. In particular examples disclosed herein, the detectable marker is a colored agent (such as colored latex, gold or carbon particle or a fluorescent molecule) to which a binder (such as streptavidin) is attached. The detectable marker can migrate independently of the target (such as the conjugate) that it is intended to label, but the detectable marker associates with the target during the assay.

Effective amount: The amount of an agent (such as an IBP) that alone, or together with one or more additional agents, induces the desired response, such as, for example binding of iodide.

Flow path: A path for a liquid to transit. Typically, the test device includes a flow path from a sample receiving zone to an iodide capture zone. The flow path is generally axial, although other configurations are acceptable and may be preferred for some embodiments. The flow path may be superficially on the surface of a substrate (for example on a non-bibulous substrate that substantially excludes liquid flow through the matrix of the substrate), or substantially entirely within and through the substrate itself (for example, through the porous structure of a substrate that does not exclude liquid from it). For example radial, multi-lane, undulating or circular flow paths are useful in test devices that can simultaneously detect the presence of multiple analytes in a sample.

Within the overall flow path toward the capture zone, there may be separate selective paths that individual chemical components may take to achieve differential migration of the individual components for the purpose of separation of components, or temporal delay of reaction.

Freely suspendable: a state of permeation or reversible surface adherence. Substances that are freely suspendable are diffusively bound on a surface such that they are not immobilized within or upon a support matrix but are capable of being mixed or suspended in liquids placed on the support matrix. Such suspended substances are capable of migrating with liquids moving along the support matrix. (see for example PCT Publication No. WO 98/39657, incorporated by reference herein).

Immobilized: Certain binding partners (such as IBP) disclosed herein are immobilized to a solid support, for example a surface of a test device. Immobilized binding partners are associated with the test device in a manner that substantially localizes the binding partner to the location in which it is placed. For example, an IBP can be immobilized in the iodide capture zone of a test device. Immobilization can be achieved using any of a variety of techniques, for example by activating the matrix prior to placing the binding partner on it. The particular methods depend on the nature of the bibulous matrix and the particular binding pair member being immobilized. For example, a specific binding partner can be immobilized through activation of a substrate by carbonyldiimidazole, glutaraldehyde, succinic acid, or cyanogen bromide. Alternatively, particles having an immobilized specific binding pair member may be used to immobilize the specific binding pair member on the capture zone. Examples of such particles are latex beads made of polystyrene, polyacrylates and polyacrylamides that are of a sufficient size and/or weight to not migrate within the test device. The particles are capable of non-diffusive attachment of the specific binding pair member by covalent or non-covalent binding, for example through functional groups such as carboxylic acids, aldehydes, amines, thiols, hydroxyls and the like.

Iodide Binding Protein (IBP): A polypeptide that specifically binds to iodide. In some embodiments, an IBP is a vanadium-dependent iodoperoxidase.

Iodide Binding Domain: The molecular structure associated with that portion of a protein (such as an iodide binding protein) that specifically binds iodide. More particularly, the iodide binding domain may refer to a polypeptide, natural or synthetic, or nucleic acid encoding such a polypeptide, the amino acid sequence of which represents a specific (binding domain) region of an iodide binding protein, which either alone or in combination with other domains, exhibits specific iodide binding characteristics that are the same or similar to those of a desired iodide/iodide binding protein binding pair. Neither the specific sequences nor the specific boundaries of such domains are critical, so long as iodide binding activity is exhibited. Likewise, used in this context, binding characteristics necessarily includes a range of affinities, avidities and specificities, and combinations thereof, so long as iodide binding activity is exhibited.

Iodide Status in a Subject: The condition of iodine level in a subject, for example, a subject can have a deficient, normal or overabundant iodide level. In several embodiments, the iodine level in a subject is detected by detecting the iodide concentration in a saliva sample from the subject.

Iodine deficiency is a condition of lower than normal iodine level in a subject. A subject with iodine deficiency is at risk of developing or having an iodine deficiency disorder (IDD). Iodine deficiency in a subject can be detected by detecting the iodide concentration in a saliva sample from the subject. A saliva concentration of less than about 75 μg per liter identifies the subject as having iodine deficiency.

Iodine deficiency disorders include a variety of conditions associated with deficient iodine intake. These disorders range from goiters and mild neurologic deficiencies to overt mental and physician retardation and cretinism. Iodine deficiency remains the leading cause of preventable mental retardation worldwide. The person of skill in the art is familiar with IDDs as well as methods of detecting and identifying symptoms of such disorders.

Iodine overabundance is a condition of greater than normal iodine level in a subject. A subject with iodine overabundance is at risk of developing or having an iodine toxicity. Iodine overabundance in a subject can be detected by detecting the iodide concentration in a saliva sample from the subject. A saliva concentration of greater than about 150 μg per liter identifies the subject as having iodine overabundance.

Lateral flow strip: A test strip, such as for use in lateral flow chromatography, in which a test sample fluid, such as a saliva sample, suspected of containing an analyte, such as iodide, flows (for example by capillary action) through the strip (which is frequently made of materials such as paper or nitrocellulose). The test fluid and any suspended analyte can flow along the strip to a detection and/or binding zone where the presence or absence of the analyte is signaled.

Lateral flow device: Devices that include bibulous or non-bibulous matrices capable of transporting analytes and reagents to a pre-selected site. Many such devices are known, in which the strips are made of nitrocellulose, paper, cellulose, and other bibulous materials. Non-bibulous materials can be used, and rendered bibulous by applying a surfactant to the material. The bibulous matrices typical are porous strips through which liquid is transported. The porous structure of such strips provides a flow path through the matrix for conducting the flow of liquid.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors including an amplified or assembled nucleic acid which can be used to transform a suitable host cell. A host cell that includes the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide.

Peptide modifications: Polypeptides, such as IBPs that specifically bind to iodide, include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer- Assisted Modeling of Drugs", in Kiegerman & Groves, eds., 1993, *Pharmaceutical Biotechnology*, Interpharm Press, Buffalo Grove, Ill., pp. 165-174 and *Principles of Pharmacology Munson* (ed.) 1995, Ch. 102, for descriptions of techniques used in CADD. Also included are mimetics prepared using such techniques.

Polypeptide: Any chain of amino acids, regardless of length or post-translational modification (e.g., glycosylation or phosphorylation). In one embodiment, the polypeptide is a disclosed antibody or a fragment thereof. A "residue" refers to an amino acid or amino acid mimetic incorporated in a polypeptide by an amide bond or amide bond mimetic. A polypeptide has an amino terminal (N-terminal) end and a carboxy terminal end.

Saliva stimulation agent: an agent that stimulates saliva production. Such agents are familiar to the skilled artisan. For example, saliva stimulation agents include sialagogues, such as citric acid.

Sample collection apparatus: A component for use in collecting a saliva sample. The sample collection apparatus can include any shape, size or material useful to facilitate collection of the saliva sample. Exemplary materials include paper, plastic and cotton. At least a portion of the sample collection apparatus is typically designed for placement in the mouth of a subject. For example, the sample collection apparatus can include a cotton swab for placement in the mouth and absorption of saliva. One or more saliva stimulation agents can be included with the sample collection apparatus. Typically, the sample collection apparatus is designed to collect from about 10 μl to about one ml of saliva.

Sample receiving zone: An area of a test device on which a liquid sample may be placed, for example to perform a test assay for iodide in the liquid saliva sample. In disclosed embodiments, the sample receiving zone is coupled to the iodide capture zone. In some disclosed embodiments the sample-receiving zone is spaced from, and upstream from the iodide capture zone. However, in other embodiments it may have a common border with the iodide capture zone.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, CABIOS 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Specifically bind: When referring to an IBP, refers to a binding reaction which determines the presence of a target moiety (such as iodide) in the presence of a heterogeneous population of proteins and other biologics. Thus, under designated conditions, an IBP binds preferentially to a particular target moiety (such as iodide) and does not bind in a significant amount to other moieties present in the sample or subject (such as chloride or bromide). Specific binding can be determined by methods known in the art. In some embodiments, with reference to an IBP/iodide complexes, specific binding of the iodide and IBP has a $K_d$ of less than about $10^{-3}$ Molar, such as less than about $10^{-3}$, Molar, $10^{-4}$ Molar, $10^{-5}$ Molar, $10^{-6}$ Molar, $10^{-7}$ Molar, $10^{-8}$ Molar, $10^{-9}$, or even less than about $10^{-10}$ Molar.

Subject: Living multi-cellular vertebrate organisms, a category that includes both human and veterinary subjects, including human and non-human mammals.

Under conditions sufficient for: A phrase that is used to describe any environment that permits a desired activity. In one example the desired activity is formation of an immune complex. In another example, the desired activity is peroxidase-catalyzed formation of a covalent bond between a tyramide and a phenol moiety, for example catalysis that occurs in the presence of hydrogen peroxide.

Vanadium-dependent iodoperoxidase (vIPO): An iodide specific peroxidase, including catalytically active and inactive forms of such a peroxidase. Exemplary vIPOs have been cloned from the brown algae species, *Laminaria digitata* (see, e.g., Colin et al., *J. Biol. Inorg. Chem.*; 10:156-166, 2005, and Int. App. Pub. No. WO2004/078976; each of which is incorporated by reference herein). In several embodiments, vIPO catalytic activity is specific to iodide relative to other halogens (such as bromide or chloride) and oxidizes iodide to reactive intermediates including HOF. Catalytically active vIPO is thermostable and responsible for the tremendous iodine trapping capacity of *Laminaria digitata*, allowing it to sequester iodine up to 0.2% of its dry weight. vIPOs specifically binds to iodide. As used herein, "vIPO" includes catalytically inactive vIPOs that specifically bind to iodide, but have reduced catalytic activity. Iodide ($X^-$) binding to vanadium (V) dependent iodoperoxidase is illustrated below.

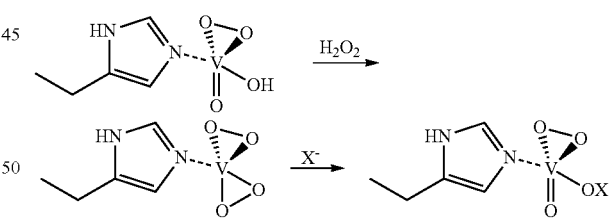

III. Methods of Detecting Iodine Deficiency in a Subject

Disclosed herein are methods of detecting iodine status in a subject, for example, detecting deficient, normal or overabundant iodine status in a subject. The amount of iodine released into saliva from the salivary gland is dependent on the amount stored in the gland and the rate at which saliva is released. In saliva, iodine is present as a halide: iodide. The concentration of iodide in saliva remains substantially constant despite variations in the production and secretion of saliva from the salivary gland. Thus, the saliva iodide concentration can be used to estimate the iodine level in the subject and detect iodine status in a subject, for example to detect if a subject has iodine deficiency. The disclosed methods include detecting binding of iodide in a saliva sample from a subject to an iodide binding protein (IBP). Detecting such binding facilitates detection of the amount and/or concentration of iodide in the saliva sample, which information can be used to detect the iodine status in the subject.

Thus, the methods include contacting a saliva sample from a subject with an effective amount of an IBP; detecting iodide binding to the IBP; and comparing the detected iodide binding to the IBP with a control, wherein comparing the detected binding of iodide to the IBP with a control identifies the iodine status in the subject. In several embodiments, comparing the detected binding of iodide to the IBP with a control identifies the iodide concentration in the saliva sample. Identification of the iodide concentration in the saliva sample can be used to detect the iodine status in the subject, for example to detect the iodine status as deficient, normal or overabundant.

A. Saliva Samples

The provided methods utilize saliva samples. A saliva sample is typically obtained from a mammalian subject of interest, such as human. Saliva samples can be obtained from a subject using any method known in the art. In some embodiments, the rate of saliva production by the subject can be increased to assist with collection of the saliva sample. Methods of increasing saliva production in a subject are known to the skilled artisan, for example saliva production can be increased by administering a sialagogue such as citric acid to the subject. In one embodiment, the saliva sample is collected by placing a cotton swab (which absorbs saliva) in the mouth of the subject, wherein the cotton swab is coated with a sialagogue to increase saliva production in the subject.

The sample can include any volume of saliva. The sample can be a frozen sample. In several embodiments, a saliva sample is collected from a subject and stored for a period of time, such as about 0.5, 1, 2, 3, 4, 5, 10, 12, 24, 36 or 48 hours, or more time, such as about 1, 2, 3, 4, 5 or 10 weeks or longer. In several embodiments, the saliva sample is collected from a subject and frozen.

In some embodiments, the saliva sample is obtained from a subject that has, is suspected of having, or is at risk of developing iodine deficiency. In several embodiments, the saliva sample is collected from a subject known to have, suspected of having, or at risk of developing, an iodine deficiency disorder. For example, the saliva sample can be collected from a subject exhibiting one or more symptoms of an iodine deficiency disorder. The person of skill in the art is familiar with the symptoms of iodine deficiency disorders, and means for recognizing such symptoms in a subject.

B. Iodide Binding Proteins

Several embodiments include an iodide binding protein (IBP) that specifically binds to iodide. In some embodiments, the IBP includes a vanadium dependent iodoperoxidase (vIPO), such as a vIPO including an amino acid sequence set forth as SEQ ID NO: 1 or SEQ ID NO: 3. In some embodiments, the IBP includes an iodide binding domain from a vIPO that specifically binds to iodide. In several embodiments the IBP includes a catalytically inactive vIPO that specifically binds to iodide. These polypeptides specifically bind to iodide, and thus can be used to capture iodide in a saliva sample.

In some embodiments, the vIPO is catalytically inactive. Examples of catalytically inactive vIPOs are known to the skilled artisan (see, e.g., Adak et al., "an essential role of active site arginine residue in iodide binding and histidine residue in electron transfer for iodide oxidation by horseradish peroxidase," *Molecular and Cellular Biochemistry* 218: 1-11, 2001; incorporated by reference herein). "Catalytically inactive" does not require that the vIPO have no iodoperoxidase activity. For example, a catalytically inactive vIPO may have at most 5, 10, 20, 30, 40, 50, 60, 70, 80, 90 or 95% of the catalytic activity of a wild-type vIPO under similar conditions (e.g., temperature, pH, buffer conditions). In some embodiments, the catalytically inactive vIPO includes an amino acid substitution of the active site histidine residue (such as histidine 483 of SEQ ID NO: 1 or histidines 407 and 476 of SEQ ID NO: 3). For example, the active site histidine residue of the vIPO can be substituted with a Alanine, Isoleucine, Arginine, Leucine, Asparagine, Lysine, Aspartic acid, Methionine, Cysteine, Phenylalanine, Glutamic acid, Threonine, Glutamine, Tryptophan, Glycine, Valine, Proline, Serine or Tyrosine residue.

One of skill will realize that conservative variants of the vIPO can be produced. Such conservative will retain critical amino acid residues necessary for correct folding and stabilizing of the vIPO, and will retain the iodide binding activity of the vIPO. Thus, amino acid substitutions (such as at most one, at most two, at most three, at most four, or at most five amino acid substitutions) can be made in the IBP. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Thus, the IBP can include a vIPO having one or more conservative amino acid substitutions, such as about 1, 2, 3, 4, 5, 6, 7, 8, 9, 10, 15, 20, 30, 40 or 50 or more conservative amino acid substitutions. In some embodiments, the IBP can include a vIPO having at most 1, 2, 3, 4, 5, 6, 7, 8, 9, 10, 15, 20, 30, 40 or 50 conservative amino acid substitutions. Thus, one of skill will recognize that the sequence of the IBP can be altered without substantially altering iodide binding activity of the IBP (e.g., by conservative substitutions).

In some embodiments, the IBP includes a vIPO (or iodide binding domain thereof). In several embodiments, the IBP includes a vIPO comprising a polypeptide having at least about 70, 80, 85, 90, 95, 96, 97, 98 or 99% sequence identity with a polypeptide including the amino acid sequence set forth as SEQ ID NO: 1 or SEQ ID NO: 3, or an iodide binding domain thereof, that specifically binds to iodide. In other embodiments, the vIPO includes the amino acid sequence set forth as SEQ ID NO: 1 or SEQ ID NO: 3. In additional embodiments, the vIPO consists of the amino acid sequence set forth as SEQ ID NO: 1 or SEQ ID NO: 3. In some such embodiments, the vIPO is catalytically inactive.

The skilled artisan can use known structural features of peroxidase enzymes, including vanadium-dependent peroxidases, such as vIPO, to select vIPO amino acid residues that can be altered (e.g., by conservative amino acid substitution) without substantially altering the iodide binding ability of the vIPO. Thus, methods of identifying vIPO amino acids that can be substituted without substantially altering the binding affinity of vIPO for iodide are known to the skilled artisan, and can, for example, be based on the three dimensional structure of an exemplary vIPO (see Int. Pat. App. Pub. No. WO2004/078976, incorporated by reference herein). The vanadium dependent peroxidases share highly a conserved binding center for vanadium on the N-terminal side of an α-helix that includes the proposed catalytic histidine residue (His418$^{V\text{-}BPO}$/His404$^{V\text{-}CPO}$/His407,476,483$^{V\text{-}IPO}$. Further, certain amino acid residues of vIPO are known to be involved with the iodide binding and/or oxidation activity of vIPO. For example, the type and position of some amino acid residues of SEQ ID NO: 1 known to be involved in iodide binding to vIPO or iodide oxidation by vIPO are shown in Table 1. Corresponding amino acid residues of other vIPOs (such as a vIPO including an amino acid sequence set forth as SEQ ID NO: 3) can be determined by the skilled artisan. In addition, conservative modifications (e.g., substitutions, additions, and deletions) can be made to facilitate proper refolding, purification, and the like, as desired.

Table 1.

Type and position of amino acid residues of SEQ ID NO: 1 known to be involved in iodide binding to vIPO or iodide oxidation by vIPO.

| Type of amino acid | Amino acid position in SEQ ID NO: 1 |
|---|---|
| Alanine | 206, 207, 215, 288, 311, 331, 357, 414, 481 |
| Arginine | 216, 411, 444, 549 |
| Aspartic Acid | 333, 348, 350 |
| Histidine | 407, 476, 483, 555 |
| Tryptophan | 400 |
| Lysine | 299, 403 |
| Phenylalanine | 200, 228, 285 |
| Proline | 289, 412, 470 |
| Serine | 300, 434 |
| Isoleucine | 301 |
| Leucine | 441, 442, 435, 436 |

In several embodiments, the IBP includes an iodide binding domain, such as functional fragment of an IBP that specifically binds to iodide. For example the iodide binding domain can include a functional fragment of a vIPO that retains specific binding activity for iodide. Methods of identifying iodide binding domains are known to the skilled artisan, and can, for example, be based on the three dimensional structure of an exemplary vIPO (see Int. Pat. App. Pub. No. WO2004/078976, incorporated by reference herein).

For example, the iodide binding domain can include about 10-620 amino acids, for example about 100-200, about 200-300, about 300-400 or more amino acids of a vIPO, such as a vIPO including a polypeptide sequence set forth as SEQ ID NO: 1 or SEQ ID NO: 3. For example, the iodide binding domain can include at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610 or 620 amino acids of a vIPO, such as a vIPO having a polypeptide sequence set forth as SEQ ID NO: 1 or SEQ ID NO: 3. Methods of identifying an iodide binding domain of a vIPO are known to the skilled artisan. In some embodiments, the iodide binding domain includes amino acids 282-624 of SEQ ID NO: 1 (disclosed as SEQ ID NO: 19 in Int. Pat. App. Pub. No. WO2004/078976). In several embodiments wherein the iodide binding domain is a functional fragment of a vIPO that specifically binds to iodide, the iodide binding domain lacks iodoperoxidase activity, for example, because of an amino acid substitution that renders the iodide binding domain catalytically inactive.

In several embodiments, an IBP is included in a fusion protein. For example, the fusion protein can include an IBP and a second heterologous moiety, such as a myc protein, an enzyme or a carrier (such as a hepatitis carrier protein or bovine serum albumin) covalently linked to the IBP. A second heterologous moiety can be covalently or non-covalently linked to the IBP.

In additional examples, the IBP can be included in a fusion protein and can also include heterologous sequences. Thus, in several specific non-limiting examples, the IBP is included in a fusion polypeptide, for example a fusion of an IBP with six sequential histidine residues, a β-galactosidase amino acid sequence, or an immunoglobulin amino acid sequence. The IBP can also be covalently linked to a carrier.

The IBP can be produced using molecular genetic techniques. For example, nucleic acid encoding an IBP can be inserted into an expression vector, the expression vector introduced into a host cell, followed by isolating the IBP. Nucleic acid molecules encoding the IBPs can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same effector molecule, detectable marker or antibody sequence.

Nucleic acid sequences encoding the IBPs can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template.

Exemplary nucleic acids including sequences encoding an IBP as described herein can be prepared by cloning techniques. Examples of appropriate cloning and sequencing techniques, and instructions sufficient to direct persons of skill through cloning are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill in the art.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill in the art.

In one example, an IBP is prepared by inserting the cDNA which encodes the IBP into a vector which includes the cDNA encoding a detectable marker, such as an enzyme or label. The insertion is made so that the IBP and the detectable marker are read in frame so that one continuous polypeptide is produced. Thus, the encoded polypeptide contains a functional IBP and a functional detectable marker region. In several examples, cDNA encoding a detectable marker, such as horseradish peroxidase or alkaline phosphatase, or a polypeptide marker of interest, is ligated to a cDNA encoding an IBP so that the detectable marker (e.g., the enzyme or polypeptide marker) is located at the amino terminus of the IBP. In another example, the detectable marker is located at the carboxyl terminus of the IBP.

Once the nucleic acids encoding the IBP are isolated and cloned, the protein can be expressed in a recombinantly engineered cell such as bacteria, plant, yeast, insect and mammalian cells using a suitable expression vector system. One or more DNA sequences encoding the IBP can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Isolation and purification of recombinantly expressed polypeptide can be carried out by conventional means including preparative chromatography and immunological separations. Once expressed, the conjugate, antibody, or antigen binding fragment thereof, can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

In addition to recombinant methods, the IBP can be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A.* pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

The IBPs can be conjugated to an agent, such as a detectable marker, including FRET acceptor and FRET donors, using any number of means known to those of skill in the art. Both covalent and noncovalent attachment means may be used. Conjugates include, but are not limited to, molecules in which there is a covalent linkage of a detectable marker to an IBP.

The detectable marker can be used to locate and/or quantify the target to which the specific binding molecule is directed (for example, iodide specifically bound to an IBP. Thereby, the presence and/or concentration of the target in a sample can be detected by detecting the signal produced by the detectable label. A detectable marker can be detected directly or indirectly, and several different detectable labels conjugated to different specific-binding molecules can be used in combination to detect one or more targets. For example, a first detectable marker, such as a hapten conjugated to an IBP that specifically binds to iodide, can be detected indirectly by using a second detectable marker that is conjugated to a molecule that specifically binds the first detectable marker.

Detectable markers include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Particular examples of detectable labels include: enzymes, such as horseradish peroxidase, alkaline phosphatase, acid phosphatase, glucose oxidase, β-galactosidase or β-glucuronidase; fluorophores (many additional examples of fluorescent molecules can be found in The Handbook—A Guide to Fluorescent Probes and Labeling Technologies, Molecular Probes, Eugene, Oreg.); nanoparticles, such as quantum dots (U.S. Pat. Nos. 6,815,064, 6,682,596 and 6,649,138, each of which patents is incorporated by reference herein); metal chelates, such as DOTA and DPTA chelates of radioactive or paramagnetic metal ions like $Gd^{3+}$; chromogens; and liposomes, for example, liposomes containing trapped fluorescent molecules.

Where the detectable marker includes an enzyme, a detectable substrate such as a chromogen, a fluorogenic compound, or a luminogenic compound is used in combination with the enzyme to generate a detectable signal (a wide variety of such compounds are commercially available, for example, from Life Technologies, Carlsbad, Calif.).

Alternatively, an enzyme can be used in a metallographic detection scheme. Metallographic detection methods include using an enzyme, such as alkaline phosphatase, in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, U.S. patent application Ser. No. 11/015,646, filed Dec. 20, 2004, PCT Publication No. 2005/003777 and U.S. Patent Application Publication No. 2004/0265922; each of which is incorporated by reference herein). Metallographic detection methods include using an oxidoreductase enzyme (such as horseradish peroxidase (HRP)) along with a water soluble metal ion, an oxidizing agent and a reducing agent, again to form a detectable precipitate (see, for example, U.S. Pat. No. 6,670,113, which is incorporated by reference herein).

Detectable markers can be linked to an IBP of interest using any number of means known to those of skill in the art. Both covalent and noncovalent attachment means may be used. The procedure for attaching a detectable marker to an IBP varies according to the chemical structure of the detectable marker. Polypeptides typically contain a variety of functional groups; such as carboxylic acid (COOH), free amine (—$NH_2$) or sulfhydryl (—SH) groups, which are available for reaction with a suitable functional group on a IBP to result in the binding of the detectable marker. Alternatively, the IBP is derivatized to expose or attach additional reactive functional groups. The derivatization may involve attachment of any of a number of known linker molecules such as those available from Pierce Chemical Company, Rockford, Ill. The linker can be any molecule used to join the IBP to the detectable marker. The linker is capable of forming covalent bonds to both the IBP and to the detectable marker. Suitable linkers are well known to those of skill in the art and include, but are not limited to, straight or branched-chain carbon linkers, heterocyclic carbon linkers, or peptide linkers. Where the IBP and the detectable marker are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the detectable marker from the IBP when the conjugate has reached its target site. Therefore, in these circumstances, conjugates will include linkages that are cleavable in the vicinity of the target site. Cleavage of the linker to release the detectable marker from the IBP may be prompted by enzymatic activity or conditions to which the conjugate is subjected in the vicinity of the target site.

In view of the large number of methods that have been reported for attaching a detectable marker to a protein, one skilled in the art will be able to determine a suitable method for attaching a given agent to an antibody or other polypeptide.

Means of detecting detectable markers are well known to those of skill in the art. Thus, for example, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

C. Contacting the Saliva Sample with an IBP

The saliva sample is contacted with an effective amount of the IBP, such that iodide in the saliva sample (if present) will specifically bind to the IBP. Methods and materials for contacting a saliva sample from a subject with an iodide binding protein are familiar to the skilled artisan and further disclosed herein.

The skilled artisan is familiar with determining the effective amount of an IBP to use depending on specific conditions under which the saliva sample is contacted with the IBP. For example, the saliva sample can be contacted with about 1 pg to about 1 g IBP. For example, the saliva sample can be contacted with about 1 pg to 500 pg, 500 pg to 1 ng, 1 ng to 500 ng, 500 ng to 1 µg, 1 µg to 500 µg, 500 µg to 1 mg, 1 mg to 500 mg or 500 mg to 1 g or more IBP.

The conditions under which the saliva sample is contacted with the IBP are sufficient for specific binding to the IBP to iodide present in the saliva sample. Conditions sufficient for iodide to specifically bind to the IBP are known to the skilled artisan and disclosed herein. For example, in some embodiments, the saliva sample is added directly to the IBP without dilution or modification. In some embodiments, the saliva sample is collected from a subject and modified before the sample is contacted with the IBP. For example, the pH, salinity, temperature, volume, buffer, or other characteristics of the saliva sample can be modified. In some embodiments, hydrogen peroxide and/or vanadium are added to the saliva sample before or during contact with the IBP.

In some embodiments, the pH of the saliva sample is modified before or during contact with the IBP. For example, the saliva sample can be modified before or during contact with the IBP to have a pH of about 2.0 to about 10, such as a pH of about 2.0, 2.5, 3.0, 3.5, 4.0, 4.5, 5.0, 5.5, 6.0, 6.5, 7.0, 7.5, 8.0, 8.5, 9.0, 9.5, or about 10.0. In some embodiments the pH of the saliva sample is not uniform throughout the saliva sample, or the pH of the saliva sample may change over the time that the sample is incubated with the IBP. The pH of the saliva sample may be altered, for example, by adding acid or base to the sample. Specifically, acids may be added to neutralize the basic pH of the native saliva to facilitate iodide binding to the IBD.

In several embodiments, the IBP is conjugated to a solid support, for example a described herein, and the saliva sample is brought into contact with the solid support such that the saliva sample contacts the IBP.

The skilled artisan will appreciate that certain variables may be considered to optimize iodide binding to the IBP and/or detection of iodide binding to the IBP (discussed below), including the chemical properties of the saliva sample, the length of time the IBP is contacted with the saliva sample, the volume of the saliva sample relative the amount of IBP contacted with the saliva sample, the concentration of iodide in the saliva sample, the solid support to which the IBP is conjugated (if used), the temperature and pH of the saliva sample and the particular detection system utilized. The skilled artisan will appreciate that these variables can be adjusted to increase binding of iodide to the IBP or detection of iodide binding to the IBP, for example, based upon a comparison of the amount of iodide detected using the provided methods compared to the amount of iodide in a control sample or control detection assay. Hence, the above variables can be adjusted as needed in increasing iodide binding to the IBP or detection of iodide binding to the IBP.

D. Detecting Iodide Binding to the IBP

Binding of iodide to the IBP can be detected and used to estimate iodide content in the saliva sample with various detection systems known in the art and described herein. In some examples, detection systems are based on conformational changes of the IBP in response to iodide binding. Such conformation changes can be detected, for example, using Förster resonance energy transfer (FRET), one of several non-labeled optical biosensing methods, gold nanoparticles or "sandwich" binding assays involving multiple iodide binding proteins.

Non-limiting optical biosensing methods for detecting the binding of iodine to a IBP to produce a detectable signal include surface plasmon resonance (SPR) sensor configurations based on, for example, coupling of optical beams to a sensor via prism coupling, waveguide coupling, optical fiber coupling, side-polished fiber coupling, and grating coupling. Both long range and short-range surface plasmon resonance (LRSP and SRSP) can be used. In embodiments wherein iodide binding to the IBP is detected using surface plasmon resonance, the IBP is typically conjugated to a solid support, for example using methods known to the skilled artisan or described herein. In some embodiments, the solid support includes a planar metal surface for use in detecting surface plasmon resonance (such as a gold or silver planar metal surface), and the IBP is immobilized to the planar metal surface, and binding of iodide to the IBP can be detected using surface plasmon resonance. Representative examples of such systems and materials for use to detect iodide binding to IBP using surface plasmon resonance are described, for example, in U.S. Pat. Nos. 4,889,427, 7,593,110, 7,671,995, 7,701,582, 7,705,990, 7,846,396, 7,791,730, 7,754,493, 7,723,122, 8,060,328, 8,094,316, all of which are incorporated herein by reference. Further, representative examples of such systems and materials for use to detect iodide binding to IBP using surface plasmon resonance are described, for example, in U.S. Patent Application Publications 20090103851 and 20100128273, both of which are incorporated herein by reference. In addition, systems based on second harmonic generation can be used to detect and quantify conformational changes associated with iodine binding.

In another embodiment, iodine binding to the IBP is detected using a gold nanoparticle aggregation assay. In such assays, positively charged moieties prevent aggregation of gold nanoparticles. In the absence of the positively charged moiety, the gold nanoparticles aggregate, which can be detected using various methods, including visual inspection. Thus, gold nanoparticle assays can be used to detect the presence of a binding pair that includes positively and negatively charged binding members. In the presence of the positively charged member of the binding pair, the gold nanoparticles will not aggregate; however, if the negatively charges member of the binding pair is also present, and binds to the positively charged member, then the positively charged member is unavailable to bind to the gold nanoparticles, which will aggregate. Thus, in some embodiments, binding of iodide (which has a negative charge and interacts with positively charged histidine residues on the IBP) to the IBP prevents binding of the IBP to the gold nanoparticles, resulting in aggregation of the gold nanoparticles. this aggregation can be detected (for example, using visual inspection) to detect binding of iodide from the saliva sample to the IBP. The skilled artisan is familiar with gold nanoparticle assays, and sources for reagents for use in such assays (see, e.g., Xia et al., *Proc. Nat'l. Acad. Sci. USA*, 107:10837-10841, 2010).

In some embodiments, binding of iodide to the IBP can be detected using a "sandwich assay," wherein iodide bound to the IBP is detected by using a binding agent that specifically binds to the complex of the iodide bound to the IBP, that is labeled with a detectable marker. In several embodiments, the binding agent that specifically binds to the complex of the iodide bound to the IBP is an IBP that is labeled with a detectable marker. Thus, in some embodiments, the saliva sample is contacted with a IBP that specifically binds to iodide under conditions sufficient for iodide binding to the IBP. The IBP (bound to iodide from the saliva sample) is isolated from the saliva sample, for example by a washing step, and then contacted with an IBP that is labeled with a detectable marker, for example as described herein. The IBP labeled with the detectable marker specifically binds to the IBP specifically bound to the iodide, resulting in a "sandwich" of (IBP)-(iodide)-(IBP)-(detectable marker). Formation of the sandwich can be detected using the detectable marker using methods known to the skilled artisan and described herein. Revelation of the detectable marker indicates formation of the sandwich, thereby detecting iodide binding to the IBP.

In some embodiments, iodide binding to the IBP is revealed by detecting a conformational change in the IBP due to iodide binding using FRET. FRET technology (see, for example, U.S. Pat. No. 4,996,143, incorporated herein by reference) is based on a photophysical process that involves non-radiative transfer of excited-state energy from an initially excited fluorescent donor to an acceptor molecule, which, if it is also a fluorescent moiety, may emit a photon at longer wavelength (Clegg et al., Biochemistry, 31:4846-4856, 1992). Thus, in embodiments in which acceptor fluorescence is measured, the acceptor is a fluorescent moiety. FRET between the members of a FRET pair can be characterized by the efficiency of energy transfer, which is measured as the relative fluorescence of the FRET donor in the presence and the absence of a corresponding FRET acceptor. As FRET occurs over a certain distance, and the efficiency of energy transfer may depend on this distance, FRET microscopy enables assessments of protein-protein interactions. Thus in particular embodiments, the IBP is labeled with a FRET acceptor and a FRET donor such that the distance between the acceptor-donor pair is altered due to iodide binding to the labeled IBP. In some examples, the distance is increased upon binding of iodide to the IBP, such that FRET can be detected between the acceptor-donor pair in the absence of iodide binding to the IBP, but not in the presence of iodide binding to IBP. In other examples, the distance is decreased upon binding of iodide to the IBP, such that FRET cannot be detected between the acceptor-donor pair in the absence of iodide binding to the IBP, but can be detected in the presence of iodide binding to IBP. The skilled artisan is familiar with methods of using FRET to detect conformational changes due to a ligand-receptor binding event.

In other embodiments, the interaction of iodine with vIPO can be quantified based on formation of reactive oxygen species resulting from the enzymatic reaction. The reactive product of this equation can be detected using a colorimetric assay or a digital readout from a semiconductor binding of the electron transfer. Electrochemical sensors can comprise a semi-conductive polymer film such as polyaniline, polythiophene, poly(3,4-ethylenedioxy)thiophene, polypyrrole, polyphenylene, polyarylene, poly(bisthiophene phenylene), poly(arylene vinylene), poly(arylene ethynylene), a conjugated ladder polymer (i.e. a polymer which requires the breaking of at least two bonds to break the chain), polyiptycene, polytriphenylene or a solid phase electron capture material such as porous silicon. An associated detection signal is produced by electrochemical and/or physical changes in the conducting polymer layer due to changes occurring at the surface of the sensor. Such systems are described in U.S. Patent Application Publication No. 2010/0248209 that is also incorporated herein by reference.

E. Comparison to a Control and Detecting Iodine Status in a Subject

Iodide binding to the IBP can be compared to a control to detect the iodine status in the subject, for example to identify the subject as having iodide deficiency. Thus, disclosed embodiments include comparing the detected binding of iodide to the IBP with a control. The control can be any suitable control against which to compare the detected binding of iodide to the IBP to detect the iodine status in the subject. In several embodiments, comparing the detected binding of iodide to the IBP with a control identifies the iodide concentration in the saliva sample, which can be used to identify the iodine status in the subject.

In some embodiments, the control is a saliva sample from a subject known not to have iodine deficiency, or a saliva sample from a subject known to have iodine deficiency. In other embodiments, the control is a reference sample, such as standard.

In other embodiments, the control is a reference value or ranges of values. For example, the reference value can be derived from the average iodide concentration in saliva samples from a group of healthy control subjects.

In some embodiments, the control is a reference value or range of values, such as a reference value calculated from the detected binding of one or more known amounts of iodide to the IBP under substantially the same conditions as the test assay. By comparing the detected binding of iodide to the IBP in the test assay to the control reference value, the concentration of iodide in the test saliva sample can be estimated. The concentration of iodide in the test sample can be used to identify the iodine status in the subject.

For example, in some embodiments, the control includes a range of reference values that reflect the surface plasmon resonance signal detected using control saliva samples with known concentrations of iodide. By comparing the surface plasmon resonance measurement of iodide binding to the IBP in the test assay to the control surface plasmon resonance measurement, the concentration of iodide in the test saliva sample is estimated. In another embodiment, the control includes a range of reference values that reflect the FRET signal detected using control saliva samples with known concentrations of iodide. By comparing the FRET measurement of iodide binding to the IBP in the test assay to the control FRET signal measurement, the concentration of iodide in the test saliva sample is estimated. In further embodiments, the control includes a range of reference values that reflect the gold nanoparticle aggregation signal detected using control saliva samples with known concentrations of iodide. By comparing the gold nanoparticle aggregation signal measurement of iodide binding to the IBP in the test assay to the control gold nanoparticle aggregation signal measurement, the concentration of iodide in the test saliva sample is estimated.

In some embodiments, the control is a reference value for the binding of iodide to the IBP that correlates with the amount of iodide in the saliva sample, wherein the amount of iodide in the saliva sample includes a range of values of iodide per liter of saliva, such as 1 to 100 ng/L, 100 to 500 ng/L, 500 to 1000 ng/L, 1 µg/L to 10 µg/L, 10 µg/L to 50 µg/L, 50 µg/L to 100 µg/L, 100 µg/L to 200 µg/L or greater ranges.

In some embodiments, a decrease in the amount of iodide specifically bound to the IBP in the test assay compared to the control amount of iodide identifies the subject as having iodine deficiency and no decrease in the amount of iodide specifically bound to the IBP in the test assay compared to the control identifies the subject as not having iodine deficiency.

The person of skill in the art is familiar with diagnostic methods of detecting iodine status in a subject based on the iodide concentration in the saliva of the subject (see, e.g., Ristic-Medic et al., *Am. J. Clin. Nutr.*, 89:2052 S-2069S, 2009. For example, in some embodiments, detecting a saliva iodide concentration in a sample from a subject of less than about 75 µg/L, such as less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 µg/L identifies the subject as having iodine deficiency. In several embodiments, detecting a saliva iodide concentration in a sample from a subject of greater than about 75 µg/L identifies the subject as not having iodine deficiency. In other embodiments, detecting a saliva iodide concentration in a sample from a subject of greater than 75 µg/L to less than 150 µg/L identifies the subject as having a normal iodine status. In further embodiments, detecting a saliva iodide concentration in a sample from a subject of greater than about 150 µg/L identifies the subject as having iodine overabundance.

In some embodiments, a score is calculated from the measurement of binding of iodide to the IBP. The score can be utilized to provide cut off points to identify subjects at low, medium, or high risk for iodine deficiency or iodine over abundance and/or low, medium, or high iodide deficiency or overabundance.

In some examples, the results of the assay are provided to a user (such as a clinician or other health care worker, laboratory personnel, or patient) in a perceivable output that provides information about the results of the analysis. In some examples, the output can be a paper output (for example, a written or printed output), a display on a screen, a graphical output (for example, a graph, chart, or other diagram), or an audible output.

In some examples, the output is a numerical value (such as an iodide concentration) in the sample or a relative amount of iodide in the sample as compared to a control. In additional examples, the output is a graphical representation, for example, a graph that indicates the value (such as amount or relative amount) of iodide in the sample from the subject on a standard curve. In a particular example, the output (such as a graphical output) shows or provides a cut-off value or concentration that indicates that subject is iodine deficient or not iodine deficient. In some examples, the output is communicated to the user, for example by providing an output via physical, audible, or electronic means (for example by mail, telephone, facsimile transmission, email, or communication to an electronic medical record).

The output can provide quantitative information (for example, an amount of iodide in the saliva sample) or can provide qualitative information (for example, a determination that the subject is iodine deficient or not iodine deficient).

IV. Devices and Systems for Use with the Disclosed Methods

Typical embodiments of a test device based on the specific binding characteristics of the IBP to identify and quantify iodide in saliva are provided. The test device can be used in the provided methods to detect the iodine status of a subject.

In several embodiments, the test device includes a sample receiving zone configured to accept a saliva sample from a subject, which is coupled to an iodide capture zone that includes an IBP as described herein. The coupling of the saliva receiving zone the iodide capture zone is configured such that the saliva sample can be mobilized from the receiving zone to the capture zone. Thus, following application of a liquid saliva sample to the sample receiving zone, the sample is mobilized to the iodide capture zone. The iodide capture zone is configured for detecting iodide binding to the IBP. Detected iodide binding to the IBP can be compared with a control using methods provided herein to determine the iodide concentration in the saliva sample and iodine status in the subject.

In some embodiments, the sample receiving zone includes a chamber capable of holding the saliva sample. In some embodiments, the chamber is configured to receive a saliva sample collected on a saliva sample collection apparatus, such as a citric acid treated cotton swab or a flexible capillary tube. In some such embodiments, the chamber includes a removable seal, e.g., a removable/replaceable plastic strip so that the saliva sample collection apparatus can be placed in the chamber and then the chamber can be resealed. In several embodiments, one or more of the walls of the chamber can be pliable so that pressure applied to the exterior of the chamber can compress the saliva sample collection apparatus so that the collected saliva sample is released into the chamber.

In some embodiments, the sample receiving zone includes an absorbent material capable of absorbing a liquid saliva sample. The sample receiving zone can be constructed of a bibulous material such as cotton or paper. In some embodiments including a sample receiving zone constructed of absorbent material, the sample receiving zone is configured to receive a definite volume of saliva, for example by adjusting the size, shape and material of the sample receiving zone.

In some embodiments, the test device includes a saliva collection apparatus to obtain a sample for analysis. The saliva collection apparatus can have various shapes and sizes. For example, a cylindrical cotton swab can be used. In another example, a capillary tube can be used. The size, shape and material of the collection apparatus can be designed to control the volume of saliva collected. Generally, saliva volumes between about 10 µl and 1 ml are satisfactory. The saliva collection apparatus can include a separate free standing device that can be placed into the test device, or can be coupled to or provided directly with the test device.

In some embodiments, the saliva collection apparatus includes a saliva stimulation reagent, such as a sialagogue, for example, citric acid. Saliva can be stimulated by coating a collection material with a sialagogue, such as citric acid. This can increase the rate of saliva production to facilitate collection of saliva from a subject. In addition, a collection apparatus can include an acidifying reagent (or other reagents) to increase iodide binding to the IBP. Citric acid is a convenient choice to act both as a sialagogue and an acidifying reagent.

The sample receiving zone is coupled to the iodide capture zone. For example, the sample receiving zone can be coupled to the iodide capture zone such that liquid saliva sample applied to the sample receiving zone transits to the iodide capture. The sample receiving zone can be coupled to the iodide capture zone via a lateral flow strip. In some embodiments, the sample receiving zone can be coupled to the binding zone via a flexible capillary tube, or via a bibulous material capable of lateral flow from the sample receiving zone to the binding zone. In several embodiments, the sample receiving zone can be coupled to the iodide capture zone via a bibulous or non-bibulous matrix that defines a liquid flow path from the sample receiving zone to the iodide capture zone, wherein application of the liquid saliva sample to the sample receiving zone results in lateral flow of the liquid saliva sample along the liquid flow path to the iodide capture zone.

The iodide capture zone includes an IBP as described herein. The amount of IBP included in the iodide capture zone will vary depending on the design of the test device. In some embodiments the iodide capture zone includes about 1 pg to 500 pg, 500 pg to 1 ng, 1 ng to 500 ng, 500 ng to 1 µg, 1 µg to 500 µg, 500 µg to 1 mg, 1 mg to 500 mg or 500 mg to 1 g or more or less IBP.

In several embodiments, the IBP included in the iodide capture zone is immobilized in the iodide capture zone. For example, a target platform within the iodide capture zone can be provided having one or more surfaces to which the IBP is immobilized, and arranged so that the surface can be exposed to the saliva sample. In other embodiments, the IBP is freely suspended in the iodide capture zone. Methods and reagents for immobilizing the IBP to the test device include standard methods known to the skilled artisan.

In several embodiments, the iodide capture zone is coupled to or includes a readout layer. In some embodiments, the readout layer includes a planar metal surface (e.g., a planar gold or silver surface) to which the IBP is immobilized, which is configured for surface plasmon measurement of iodide binding to IBP as described herein. In some such embodiments, the test device is configured such that the readout layer can be exposed to an apparatus for measuring surface plasmon resonance. In some examples, the readout layer includes portions associated with two or more readout mechanisms such as associated with conformational changes, the presence of reactive oxygen species, the presence of FRET, or colorimetric changes.

A typical example of a test device includes a citric acid coated cotton swab for placement in the mouth to stimulate and collect saliva. The volume collected can be preset by the size and capacity of the swab. A chamber is provided to receive the saliva saturated swab, and can include a soft (deformable) plastic cover that permits a user to release the saliva into the chamber by applying pressure to the cover. The device can include a zone containing recombinant IBP that is situated at or within the chamber so as to receive the released saliva to the IBP. An additional membrane, surface, or reagent volume can be provided as part of a biosensor, colorimetric sensor, or electrochemical sensor for detection of iodine binding to the IBP. For example, a suitable surface for surface plasmon resonance can be provided, or a reagent volume for colorimetric sensing can be provided.

The disclosure is illustrated by the following non-limiting Examples.

Examples

A representative test device 100 is illustrated in FIG. 1. A sample receiving chamber 102 is configured to receive a saliva sample collected on a saliva sample collection apparatus 104, such as a citric acid treated cotton swab. The chamber includes a removable seal 106 such as a removable/replaceable plastic strip so that the saliva sample collection apparatus 104 can be placed in the chamber 102 and then the chamber 102 can be resealed. One or more of the walls of the chamber 102 are preferably pliable so that pressure applied to the exterior of the chamber 102 can compress the saliva sample collection apparatus 104 so that a substantial portion of a collected saliva sample is released. A second chamber 108 includes a sensing layer 110 that can include a sensing agent such as immobilized IBP. A readout layer 112 (or readout apparatus) is also provided that is responsive to iodide binding to the IBP at sensing layer 110. In some examples, the readout layer 112 includes portions associated with two or more readout mechanisms such as associated with conformational changes or the presence of reactive oxygen species.

Figure 2:
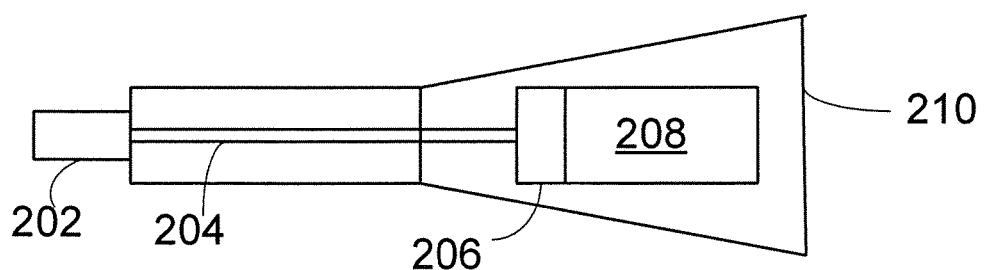
FIG. 2 is a sectional diagram of a representative IBP-based iodine sensor.

Another example test device is illustrated in FIG. 2. A saliva sample collector 202 that includes a sialagogue is coupled to a capillary tube 204 through which a saliva sample can be directed to a volume (or surface) that includes one or more IBP layers. The saliva sample collector can be compressible so that collected saliva can be directed into the tube 204. A reagent volume 208 can be provided and can contain one or more reagents responsive to bound iodine/vIPO. A colorimetric, fluorometric or other reagent can be provided in the volume 208, and a sensor housing 210 can be arranged to permit access by optical, electrical, or other readout systems based on, for example, optical absorption, fluorescence, harmonic generation, or surface plasmon resonance. The sensor housing 210, the saliva sample collector 202, and the capillary tube can be constructed inexpensively so as to be disposable.

Figure 3:
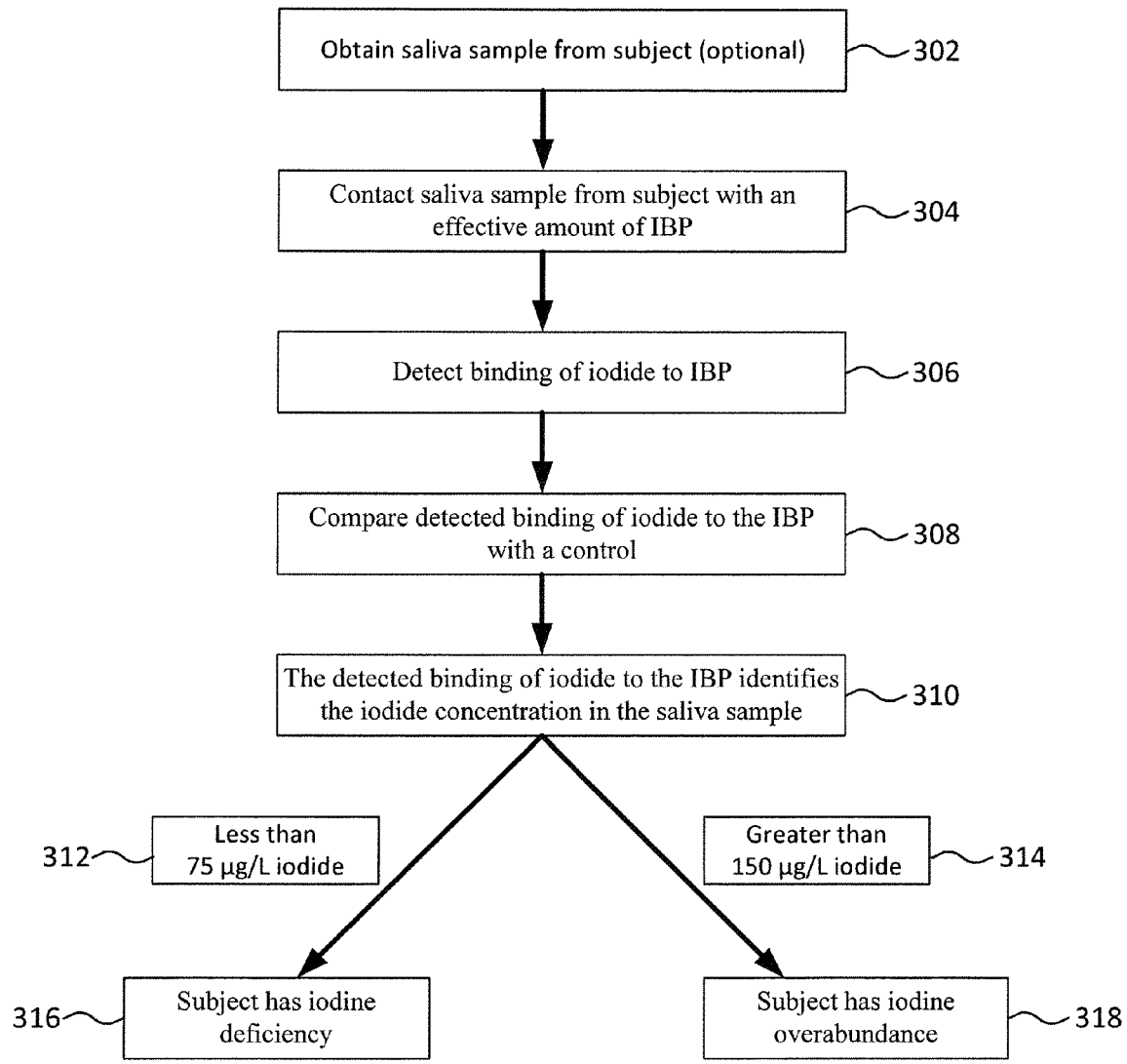
FIG. 3 is a flow chart illustrating a representative embodiment of a method of detecting iodine status in a subject.

The steps of a representative method of detecting iodine status in a subject are illustrated in FIG. 3. In optional step 302, a saliva sample is obtained from a subject. The sample can include any volume of saliva, for example about 1 ml of saliva. Saliva production in the subject can be enhanced using citric acid, for example by placing a cotton swab coated with citric acid in the mouth of the subject. The citric acid enhances saliva production in the subject and the cotton swab absorbs the saliva. The cotton swab containing the saliva can be collected; thus obtaining the saliva sample.

In step 304, a saliva sample from the subject is contacted with an effective amount of an iodide binding protein (IBP) under conditions sufficient for binding of iodide in the saliva sample to the IBP. The IBP includes an iodide binding domain of a vanadium dependent iodoperoxidase (vIPO) that has been modified, such that the iodide binding domain specifically binds to iodide, but does not catalyze the oxidation of iodide. For example, the iodide binding domain can be a protein including the amino acid sequence set forth as amino acid residues 282-624 of SEQ ID NO: 1 having a lysine residue substituted for the histidine residue at position 483 of SEQ ID NO: 1. The IBP is immobilized to a solid support, for example, a planar gold surface configured for surface plasmon resonance measurement. One ml of saliva is incubated with an effective amount of the IBP, for example the amount of IBP needed to effectively coat the surface of the planar gold surface for surface plasmon resonance measurement. In step 306, the binding of iodide in the saliva sample to the IBP is detected, for example, by detecting a change in the confirmation of the IBP immobilized on the planar gold surface using surface plasmon resonance measurement.

In step 308, the detected binding of iodide to the IBP is compared with a control. The control can be a range of reference values that reflect the surface plasmon resonance signal detected using control saliva samples with known concentrations of iodide. By comparing the surface plasmon resonance measurement of iodide binding to the IBP in the test assay to the control surface plasmon resonance measurement, the concentration of iodide in the test saliva sample is estimated, as illustrated by step 310. The concentration of iodide in the test sample can be used to identify the iodine status in the subject. For example, as illustrated by steps 312 and 316, if the concentration of iodide in the test saliva sample is less than 75 μg/L, the subject has iodine deficiency. Steps 314 and 318 illustrate that if the concentration of iodide in the test saliva sample is greater than 150 μg/L, the subject has iodine overabundance. If the iodide concentration in the test saliva sample is between 75 μg/L and 150 μg/L, then the subject has a normal iodine level.

In view of the many possible embodiments to which the principles of the disclosure may be applied, it should be recognized that the illustrated embodiments are only preferred examples and should not be taken as limiting in scope. We claim as our invention all that comes within the scope and spirit of the appended claims.

I claim:

1. A test device for detecting iodide in saliva, the test device comprising:

a sample receiving zone; and an iodide capture zone comprising an iodide binding protein that specifically binds to iodide, wherein the iodide binding protein comprises a vanadium-dependent iodoperoxidase comprising the amino acid sequence of SEQ ID NO: 1 or SEQ ID NO: 2;

wherein the sample receiving zone is coupled to the iodide capture zone, and wherein application of a liquid saliva sample to the sample receiving zone results in application of the liquid saliva sample to the iodide capture zone and binding of iodide in the liquid saliva sample to the IBP.

2. The test device of claim 1, wherein the sample receiving zone comprises a chamber capable of receiving a saliva sample.

3. The test device of claim 1, further comprising a sample collection apparatus capable of absorbing a liquid saliva sample.

4. The sample collection apparatus of claim 3, comprising a saliva stimulation agent.

5. The test device of claim 1, wherein the sample receiving zone comprises an absorbent material.

6. The test device of claim 1, wherein the sample receiving zone is coupled to the iodide capture zone by a lateral flow strip.

7. The test device of claim 6, wherein the sample receiving zone is coupled to the iodide binding zone via a capillary tube, wherein application of the liquid saliva sample to the sample receiving zone results in lateral flow of the liquid saliva sample to the iodide capture zone.

8. The test device of claim 6, wherein the sample receiving zone is coupled to the iodide binding zone via a bibulous matrix that defines a liquid flow path from the sample receiving zone to the iodide capture zone, wherein application of the liquid saliva sample to the sample receiving zone results in lateral flow of the liquid saliva sample along the liquid flow path to the iodide capture zone.

9. The test device of claim 1, wherein the iodide capture zone comprises a sensing layer and wherein the IBP is immobilized to the sensing layer.

10. The test device of claim 1, wherein
    the iodide capture zone comprises a planar metal surface for use with measuring surface plasmon resonance; and
    the IBP is immobilized to the planar metal surface; wherein iodide binding to the IBP can be detected using surface plasmon resonance.

11. The test device of claim 1, wherein the IBP is freely suspendable in the iodide capture zone.

12. The test device of claim 1, wherein the iodide capture zone comprises gold nanoparticles.

\* \* \* \* \*